US010092203B2

(12) United States Patent
Mirov

(10) Patent No.: US 10,092,203 B2
(45) Date of Patent: Oct. 9, 2018

(54) USING SKIN RESISTANCE MEASUREMENTS TO DETERMINE TIMING OF BIO-TELEMETRY MEASUREMENTS

(71) Applicant: Verily Life Sciences LLC, Mountain View, CA (US)

(72) Inventor: Russell Norman Mirov, Los Altos, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 189 days.

(21) Appl. No.: 14/833,021

(22) Filed: Aug. 21, 2015

(65) Prior Publication Data
US 2017/0049352 A1 Feb. 23, 2017

(51) Int. Cl.
*A61B 5/0408* (2006.01)
*A61B 5/00* (2006.01)
(Continued)

(52) U.S. Cl.
CPC ........ *A61B 5/04085* (2013.01); *A61B 5/0245* (2013.01); *A61B 5/02438* (2013.01); *A61B 5/0402* (2013.01); *A61B 5/0531* (2013.01); *A61B 5/0533* (2013.01); *A61B 5/681* (2013.01); *A61B 5/6824* (2013.01);
(Continued)

(58) Field of Classification Search
CPC . A61B 5/04085; A61B 5/6824; A61B 5/6825; A61B 5/6826
See application file for complete search history.

(56) References Cited

U.S. PATENT DOCUMENTS 2,635,835 A 4/1953 Dungan et al.
2,764,369 A 9/1956 Melton
(Continued)

FOREIGN PATENT DOCUMENTS

EP 0861045 B1 8/2002
WO 2013/074395 A1 5/2013
WO 2014/063160 A1 4/2014

OTHER PUBLICATIONS

International Searching Authority, International Search Report and Written Opinion for PCT/US2016/039680, dated Oct. 7, 2016.
(Continued)

*Primary Examiner* — Lee S Cohen
(74) *Attorney, Agent, or Firm* — McDonnell Boehnen Hulbert & Berghoff LLP

(57) ABSTRACT

Wearable devices are provided including electrical contacts to detect voltages or other biosignals when mounted to the skin of a wearer. The impedance between a pair of the electrical contacts can be detected and the device operated based on the detected impedance. The device can detect an electrocardiogram or other biopotentials using the electrical contacts if the detected impedance falls below a specified threshold. The device could indicate that the detected impedance is below the specified threshold, e.g., such that a wearer could contact one of the electrical contacts with a finger to allow detection of an electrocardiogram between the arms of the wearer. The device could indicate that the detected impedance remains greater than the specified threshold, e.g., such that a wearer could re-mount the wearable device to improve the electrical connection between the electrical contacts and the wearer's skin.

18 Claims, 11 Drawing Sheets

(51) Int. Cl.
*A61B 5/024* (2006.01)
*A61B 5/0245* (2006.01)
*A61B 5/0402* (2006.01)
*A61B 5/053* (2006.01)

(52) U.S. Cl.
CPC .......... *A61B 5/6843* (2013.01); *A61B 5/6885* (2013.01); *A61B 2562/0214* (2013.01)

(56) References Cited

U.S. PATENT DOCUMENTS

| | | | |
|---|---|---|---|
| 2,931,597 | A | 4/1960 | Moore, Jr. |
| 2,967,677 | A | 1/1961 | Winzen et al. |
| 3,080,138 | A | 3/1963 | Church |
| 4,120,294 | A * | 10/1978 | Wolfe .................... A61B 5/024 600/384 |
| 4,174,082 | A | 11/1979 | Eshoo |
| 4,215,834 | A | 8/1980 | Dunlap |
| 4,262,864 | A | 4/1981 | Eshoo |
| 5,738,104 | A | 4/1998 | Lo et al. |
| 5,876,350 | A | 3/1999 | Lo et al. |
| 6,540,178 | B1 | 4/2003 | Hillsdon |
| 6,950,695 | B2 * | 9/2005 | Chen .................. A61B 5/02438 600/509 |
| 7,567,779 | B2 | 7/2009 | Seligsohn et al. |
| 7,568,656 | B2 | 8/2009 | Handley |
| 8,369,936 | B2 | 2/2013 | Farringdon et al. |
| 9,526,433 | B2 * | 12/2016 | Lapetina .............. A61B 5/6824 |
| 2002/0026114 | A1 | 2/2002 | Nissila |
| 2004/0220485 | A1 | 11/2004 | Rytky |
| 2007/0063489 | A1 | 3/2007 | Dinsdale et al. |
| 2008/0272233 | A1 | 11/2008 | Marlin |
| 2009/0294576 | A1 | 12/2009 | LaForge |
| 2010/0076331 | A1 | 3/2010 | Chan et al. |
| 2014/0031704 | A1 | 1/2014 | De Vries et al. |
| 2014/0055352 | A1 | 2/2014 | Davis et al. |
| 2014/0085077 | A1 | 3/2014 | Luna et al. |
| 2015/0135310 | A1 | 5/2015 | Lee |

OTHER PUBLICATIONS

Analog Devices, Inc., Data Sheet for AD8232, "Single-Lead, Heart Rate Monitor Front End," 2012, 28 pages.
Broeders, Jan-Hein, "Predicting and Finding your Limits!," Technical Article MS-2385, Analog Devices, Inc., 2012, 3 pages.
Oregon Scientific, Heart Rate Monitor Walch with Calorie Counter, Model: IHM80004, User Manual, 2010, 2 pages.
Oregon Scientific, Touch Strapless Heart Rate Monitor, Model: SE338/SE338M, User Manual, 2011, 2 pages.
Sportline, Inc., Solo 910 Heart Rate Walch, 2006, 18 pages.
International Searching Authority, International Search Report and Written Opinion for PCT/US2013/020525 dated Apr. 22, 2013, 16 pages.

* cited by examiner

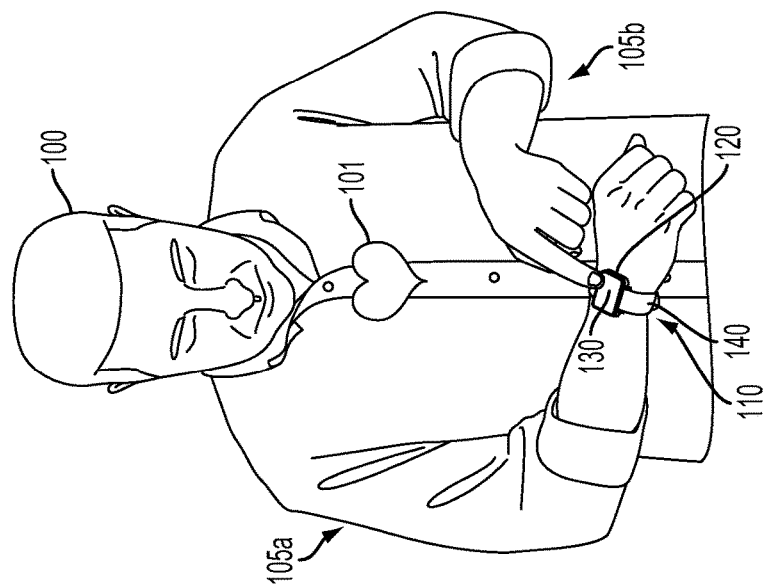
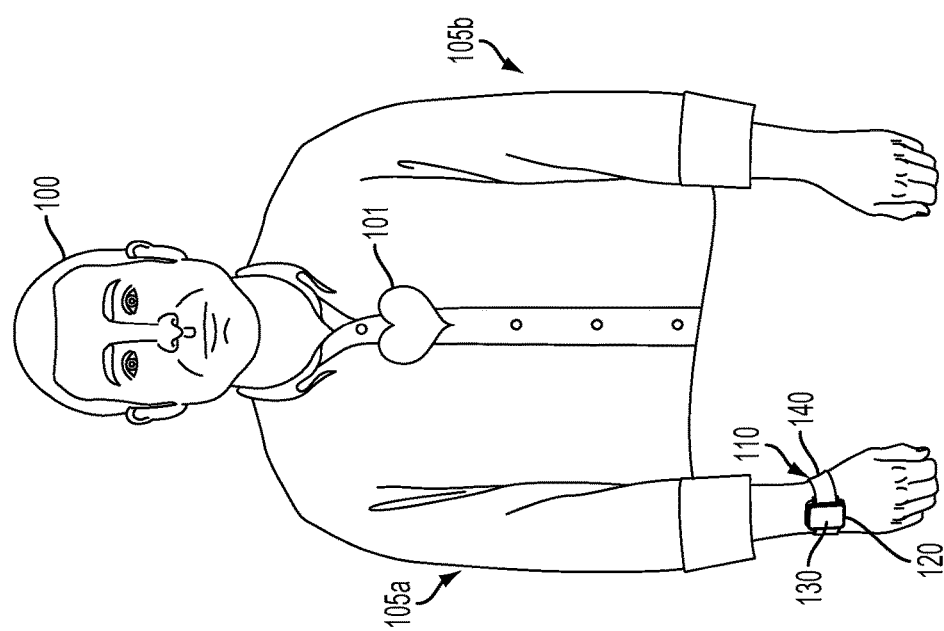

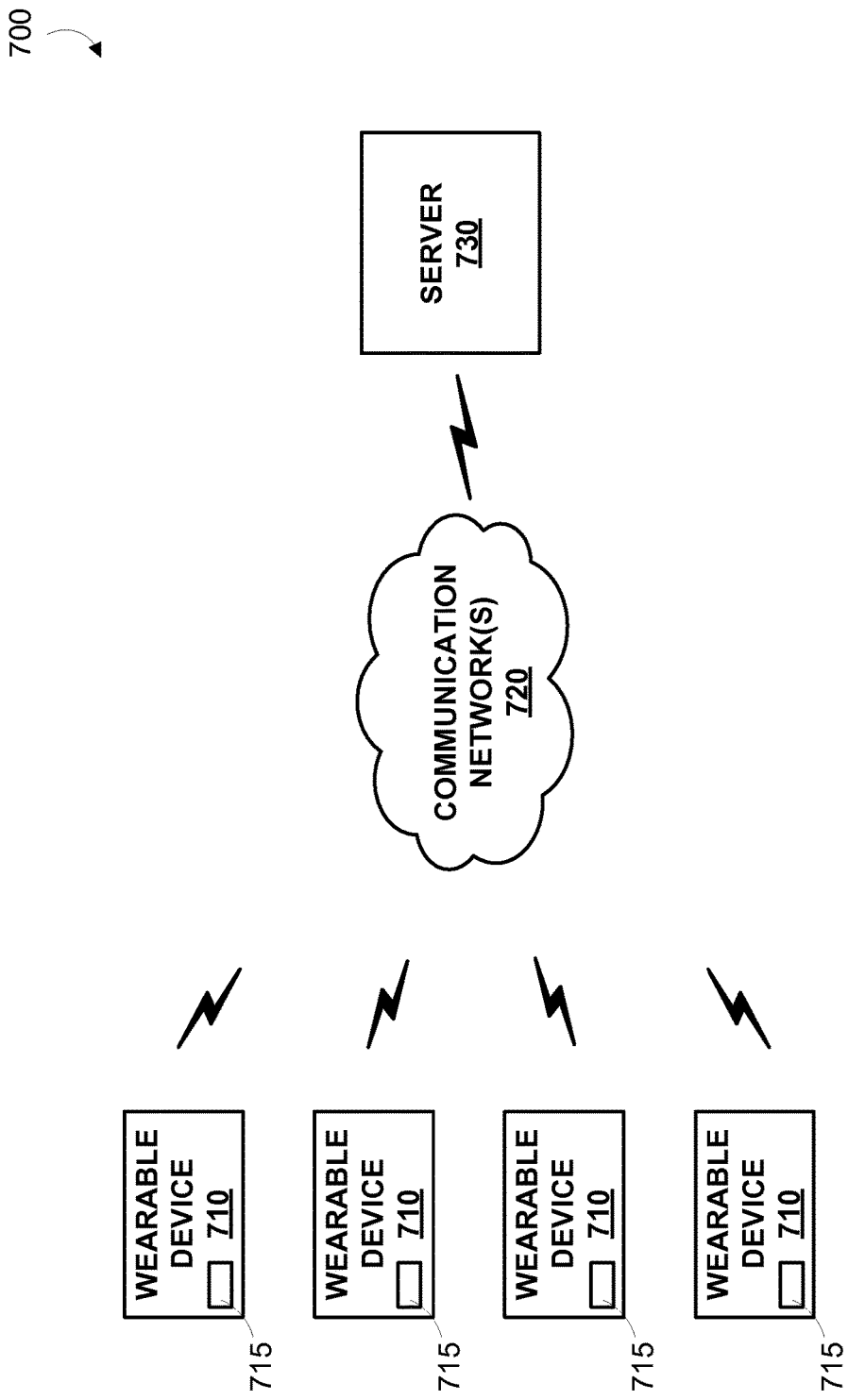

USING SKIN RESISTANCE MEASUREMENTS TO DETERMINE TIMING OF BIO-TELEMETRY MEASUREMENTS

BACKGROUND

Unless otherwise indicated herein, the materials described in this section are not prior art to the claims in this application and are not admitted to be prior art by inclusion in this section.

A variety of applications can be provided by wearable devices, e.g., devices configured to be mounted to a wrist or other location of a user's body. Such devices can provide information and/or communications functions to the user (e.g., by providing an indication of the current time or the user's location, by providing the content of an email received by the user). Such devices could include one or more sensors configured to detect properties of the user's body (e.g., a blood pressure, a heart rate, a blood oxygen saturation, electrical activity of the heart) and/or of the environment of the user (e.g., an ambient temperature, a barometric pressure) and to record, provide indications of, communicate to external systems, or otherwise use such detected properties.

SUMMARY

Some embodiments of the present disclosure provide a wearable device including: (i) a housing; (ii) a mount configured to mount the housing to a first external body surface; (iii) a first electrical contact that is disposed on the housing and that is configured to contact skin at the first external body surface when the housing is mounted on the first external body surface, wherein the first external body surface is a wrist location of a first arm of a wearer; (iv) a second electrical contact that is disposed on the housing and that is configured to contact skin at the first external body surface when the housing is mounted on the first external body surface; (v) a third electrical contact that is disposed on the housing and that is configured to be contacted by skin of a second external body surface, wherein the second external body surface is a location of a second arm of the wearer; and (vi) a controller. The controller is configured to perform controller operations including: (a) detecting an impedance between the first and second electrical contacts; (b) determining whether the detected impedance is less than a specified threshold; and (c) responsive to determining that the detected impedance is less than the specified threshold, detecting a voltage between the first electrical contact and the third electrical contact.

Some embodiments of the present disclosure provide a method including: (i) detecting an impedance between a first electrical contact and a second electrical contact of a wearable device; (ii) determining whether the detected impedance is less than a specified threshold; and (iii) responsive to determining that the detected impedance is less than the specified threshold, detecting a voltage between the first electrical contact and a third electrical contact of the wearable device. The first, second, and third electrical contacts are disposed on a housing of a wearable device that includes a mount configured to mount the housing to a first external body surface that is a wrist location of a first arm of a wearer. The first and second electrical contacts are configured to contact skin at the first external body surface when the housing is mounted on the first external body surface and the third electrical contact is configured to be contacted by skin of a second external body surface that is a location of a second arm of the wearer These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 1A is a view of a person wearing an example wearable device.

FIG. 1B is a view of the person and wearable device illustrated in FIG. 1A, when the user is contacting an electrical contact of the wearable device with a finger.

FIG. 7 is a block diagram of an example system that includes a plurality of wearable devices in communication with a server.

DETAILED DESCRIPTION

Figure 2:
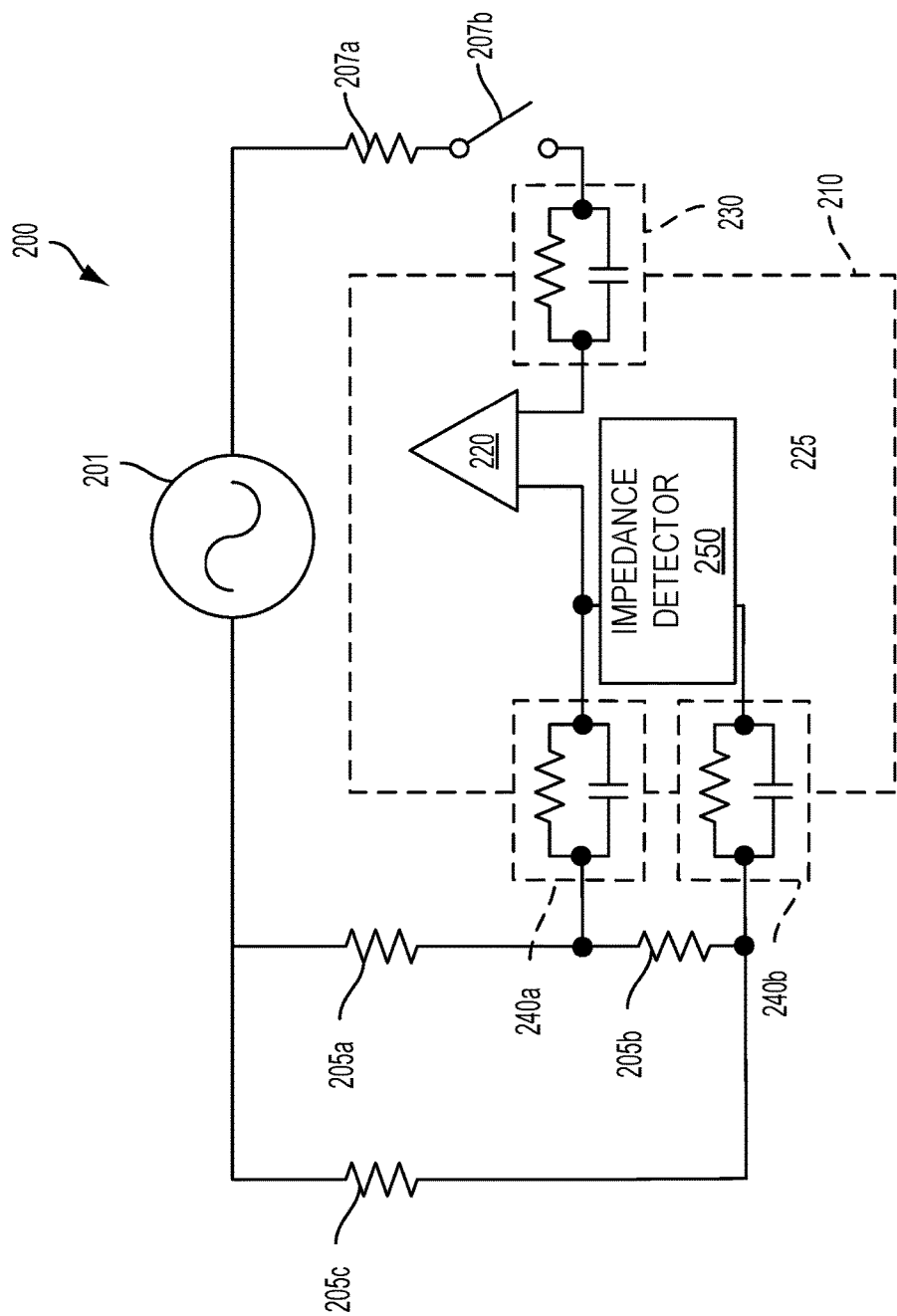
FIG. 2 is a diagram illustrating an example electrical model of elements of the person and wearable device illustrated in FIGS. 1A and 1B.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

I. Overview

A wearable device may be configured to perform a variety of different functions and/or applications. In some examples, a wearable device is configured to measure one or more physiological parameter of a wearer and/or to measure one or more properties of the environment of the wearer. A wearable device could be configured to detect physiological parameters using one or more electrical contacts configured to be mounted to a skin surface to provide an electrical connection with the skin. Two or more such electrical contacts could be used to detect properties of the skin (e.g., a skin impedance, a Galvanic skin resistance, a Galvanic skin potential), properties of the electrical connection between the electrical contact(s) and the skin (e.g., an ohmic and/or capacitive electrode impedance), or other physiological parameters (e.g., an electrocardiogram, an electromyogram, an electrooculogram, or some other biopotentials related to the activity of the heart, muscles, or other physiological parameters). Such electrical contacts could have a surface texture, a surface material (e.g., gold, silver, platinum, or some other metal or alloy, a layer of conductive gel, a layer of silver chloride over silver metal), or some other properties or materials configured to provide an electrical connection with the skin.

Electrical signals (e.g., biopotentials, currents, voltages) detected using such electrical contacts could be affected by properties of the electrical connection between the skin and the electrical contacts. Such a connection could be characterized by an impedance, e.g., a, ohmic, reactive, resistive, capacitive, inductive, or otherwise characterized electrical property describing the flow of current and/or the transfer of voltages between the skin surface and electronics or other components connected to the electrical contacts. Properties of biopotentials or other signal detected using the electrical contacts could be affected by the impedance of the electrical contacts, e.g., a signal amplitude or power, a noise amplitude or power, a signal spectral profile, a noise spectral profile, an offset voltage or some other properties of detected biopotentials or other detected signals. Such effects could further be related to properties of electronics connected to the electrical contacts, e.g., a degree of attenuation of a detected biopotential could be related to a ratio between an input impedance of an amplifier connected to the electrical contacts and the impedance between the skin and the electrical contacts.

The impedance between an electrical contact and skin and/or tissue beneath the skin could be related to a variety of factors of the skin, e.g., to a thickness of the skin, a fat content of the skin, a keratin content of the skin, a skin type (e.g., glabrous skin), a degree of moisture and/or hydration on/within the skin, a degree of perfusion of the skin, or some other properties of the skin. The impedance could change over time, e.g., the impedance could reduce over time due to accumulation of moisture (e.g., sweat or other fluids) from the skin beneath and/or proximate an electrical contact mounted to the skin.

The impedance between one or more electrical contacts and skin to which such contacts are mounted could be directly or indirectly detected by a wearable device. This could include detecting the impedance (e.g., the resistance, capacitance, inductance, reactance, impedance at one or more frequencies, impedance spectrum) between two or more such electrical contacts that are mounted to the skin. Such a detected impedance could be used to determine a physiological parameter, e.g., to determine a Galvanic skin response, a skin perfusion, a skin hydration level, or some other physiological parameters. Additionally or alternatively, the wearable device could be operated based on a detected impedance. In some examples, the wearable device could use an electrical contact to detect a biopotential (e.g., an electrocardiogram, a Galvanic skin potential, an electromyogram) when the detected impedance is less than a specified threshold (e.g., the resistive component of the impedance is below a specified threshold), e.g., such that the detected biopotential is attenuated less than a specified amount and/or such that the detection biopotential includes less than a specified amount (e.g., power) of noise. Detecting a biopotential could include detecting a voltage between two or more electrical contacts whose impedance(s) have been measured and/or detecting a voltage between one or more such electrical contacts and further electrical contacts. In some examples, a detected biopotential could be scaled (e.g., multiplied or divided) based on a detected impedance, e.g., to determine a normalized amplitude of a related biosignal or other physiological parameter within the body.

The wearable device could provide indications related to a detected impedance. For example, the wearable device could indicate that the detected impedance is above a specified threshold such that a user could reseat or otherwise alter the mounting of the wearable device on skin (e.g., such that the impedance can be reduced below the threshold level by, e.g., the deposition of moisture beneath and/or proximate to electrical contacts of the wearable device). In another example, the wearable device could be configured to be mounted to a first arm and to detect an electrocardiogram between a first electrical contact that is mounted to skin of the first arm (e.g., skin at the wrist of the first arm) and a second electrical contact that the wearer could contact with skin of a finger (or other skin surface) of a second arm. The device could detect the impedance between the first electrical contact and a third electrical contact that is mounted to skin of the first arm and an indication could be provided when the detected impedance is below a specified threshold. A user could, responsive to such an indication, place skin of the second arm (e.g., a fingertip) in contact with the second electrical contact such that an electrocardiogram can be detected using the first and second electrical contacts.

A wearable device could be operated based on a detected impedance in other ways. In some examples, a detected decrease in impedance could be used to determine whether an interface between the wearable device and the skin surface is stable (e.g., by determining that the detected impedance is less than a specified threshold and/or that the detected impedance is relatively stable over time). In such examples, a physiological parameter (e.g., a volume of blood in a portion of subsurface vasculature, a velocity or flow rate of blood in a portion of subsurface vasculature, a level of blood oxygenation in skin) could be detected (e.g., by illuminating and/or receiving light remitted from the skin) responsive to determining that the detected impedance is less than a specified threshold or satisfies some other condition(s).

An impedance between two electrical contacts can be detected in a variety of ways. In some examples, a specified voltage and/or current could be applied between/through the electrical contacts and amplitude, time dependence, or other properties of a current/voltage responsively developed through/between the electrical contacts could be detected and used to determine the impedance. The applied specified voltage and/or current could have a specified waveform or other property of variation over time, e.g., a specified frequency, pulse width, pulse repetition frequency, pulse rise time, or other properties. For example, an oscillating voltage at a specified frequency could be applied between two electrical contacts and an amplitude, relative phase, or some other property of a time-varying current responsively passing through the electrical contacts could be detected and used to determine an impedance (e.g., a magnitude, a phase, a real component, and imaginary component) between the two electrical contacts at the specified frequency. Additionally or alternatively, the applied voltage and/or current could be substantially constant (e.g., a DC voltage or current) during a specified period of time to provide for the detection of a DC impedance between the two electrical contacts.

In a particular example, a capacitor could be electrically connected between the two electrical contacts. The capacitor could be charged (e.g., charged to a specified voltage) during a first period of time and subsequently discharged through the two electrical contacts (e.g., through skin to which the electrical contacts are mounted). A voltage across and/or a current through the capacitor could be measured during the discharge to determine an impedance (e.g., a DC impedance, a phase and magnitude of an AC impedance at one or more frequencies, an impedance spectrum, a resistive, capacitive, inductive, and/or reactive component of the impedance) between the two electrical contacts. The impedance between two or more electrical contacts could be detected in some other way.

In some examples, the wearable device may include a user interface that is configured to provide user-discernible indications (e.g., visual, audible, and/or tactile indications) of information sensed by sensors of the wearable device, progress or other information related to a function of the device, or other information. In some examples, the user interface could additionally provide a means for specifying one or more settings of the wearable device (e.g., a sampling rate, a user information privacy setting, a user's credentials to access a service) according to a wearer's preferences. Indications provided by an output component (e.g., a display, a beeper, a vibrator, a speaker) could indicate information related to a detected hemodynamic parameter or other physiological parameter, e.g., a determined heart rate, a determined pulse transit time, a determined blood oxygen saturation, a determined blood pressure. In some examples, the wearable device may include a wireless communication interface that can transmit/receive data to/from an external device, for example, using Bluetooth, ZigBee, WiFi, and/or some other wireless communication protocol. The wireless communications interface could additionally or alternatively be configured to receive data from an external system (e.g., parameters relating to the operation of an energy emitter configured to emit energy into blood of the wearer to effect a change in some analyte in the blood).

The wearable device could include a mount (e.g., a strap, a belt, an enclosing member, an adhesive) configured to secure the wearable device to a wrist, neck, abdomen, ankle, or some other location of a user's body. Additionally or alternatively, embodiments described herein could be configured as other types of devices, e.g., handheld devices, benchtop devices, or otherwise configured devices. Devices as described herein (e.g., wearable devices) could be configured to removably couple to external systems, e.g., external chargers, to provide a variety of applications. For example, an external charger could provide power (e.g., power to recharge a battery of a wearable device), communications (e.g., a communications channel to download updated software, to upload recorded information, to interact with a vehicle), or some other facilities to the wearable device.

It should be understood that the above embodiments, and other embodiments described herein, are provided for explanatory purposes, and are not intended to be limiting.

II. Example Detection of Biosignals and Electrode Impedances

The impedance between one or more electrical contacts and a skin surface (or other tissue) can be related to a quality of the electrical connection between the electrical contact and the skin surface, a quality and/or stability of mounting a device that includes the electrical contact to a body surface, a property of the skin surface (e.g., a pliability, an amount of moisture on or within the skin), or other properties of a body and/or of a device mounted thereto. As such, the impedance between one or more electrical contacts and a skin surface could be detected and used to determine properties of the skin and/or the interface between the skin and the electrical contact(s), to instruct a user in the operation of a device that includes the electrical contact(s) (e.g., to indicate that the user should re-mount the device, that the user should contact the device to initiate detection of a biosignal), to control the timing or other properties of operation of the device (e.g., to control the timing of detection of a biosignal, to scale or otherwise modify such a detected biosignal), or to provide some other applications.

Impedance, as used herein, describes a relationship between a voltage between two points (e.g., between the metal or other conductive bulk material of an electrical contact and skin to which the contact is mounted) and a current flowing to (or from) the first point to the second point. The first and second points could be a point in tissue (e.g., skin) and a point electrically coupled to an electrical contact mounted to the tissue. The first and second points could be points electrically coupled to first and second electrical contacts mounted to tissue (e.g., to proximate locations on an external skin surface of a body). The impedance can be characterized by real (i.e., resistive) and reactive (i.e., capacitive) aspects, by a magnitude and a phase angle, by a single value (e.g., the resistive aspect of the detected impedance, the magnitude of the overall impedance), or in some other way. Further, the impedance can be frequency-dependent. That is, the magnitude, phase, or other aspects of the impedance between an electrical contact and tissue, or between first and second electrical contacts that are both in contact with tissue of a body, could have a first value when a time-varying voltage of a first frequency is applied and a second value when a time-varying voltage of a second frequency is applied. Thus, the impedance can be characterized as a spectrum, having a magnitude, value, or other properties that vary across a range of frequencies.

When a comparison of an impedance to some other value (e.g., a threshold) is described, this could include comparison of the overall magnitude, the magnitude of the real (resistive) component, or some other property of the impedance to the other value. Further, such a comparisons could be performed between the property of the impedance at a particular frequency (e.g., at approximately 1 kilohertz, at approximately 0 Hertz or 'DC'), across a range of frequencies (e.g., an average magnitude of the impedance across a specified range of frequencies of interest), or in some other way related to the frequency dependence of the impedance.

The impedance of a particular electrical contact mounted to tissue can be defined as the impedance between a point within the conductive material of the electrical contact and a point within the tissue. The impedance can be indirectly measured by detecting the impedance between the conductive material of the electrical contact and the conductive material of a second electrical contact (e.g., an electrode) that is also in contact with the tissue (e.g., that is penetrating the tissue). The measured impedance can be related to (e.g., a sum of) the impedances between each of the electrical contacts and the tissue and to an amount of impedance within the tissue between first and second locations of the tissue at which the electrical contacts are electrically connected to the tissue. In some examples, the second electrical contact could be configured to have a very low impedance relative to the first contact (e.g., could have a very high surface area, could be implanted into or otherwise penetrate the tissue, could include a conductive gel disposed between the electrical contact and the tissue surface) such that the detected impedance is mostly related to the impedance between the first electrical contact and the tissue. Additionally or alternatively, the impedance of the first electrical contact could be calculated as half of the detected impedance between the first and second electrical contacts, or an effective impedance between the electrical contacts, in parallel, could be calculated based on the detected impedance.

The impedance between one (or more) electrical contacts and tissue is related to a variety of factors. The impedance could be related to properties of the mounting of the electrical contact(s) and the tissue surface (e.g., a pressure applied to mount the contact(s) to the tissue, and angle between a surface of the contact(s) and the surface of the tissue). The impedance could be related to properties of the tissue surface, e.g., the presence of hair on a skin surface, an amount of moisture on a skin surface, a compliance or elasticity of a skin surface, a thickness of skin, the composition (e.g., a thickness of a low-conductivity epidermal layer) of a skin surface, a degree of vascularization and/or perfusion of skin, or some other properties of a tissue and/or tissue surface (e.g., of skin and/or of the surface thereof). The impedance could also be related to the composition and/or configuration of the electrical contact(s). For example, an electrical contact that includes a layer of silver chloride disposed on a layer of silver could have a lower impedance into skin than an electrical contact of similar size and geometry that does not include a layer of silver chloride. In another example, an electrical contact could be configured to electrically couple to a skin surface capacitively (e.g., by including a thin layer of dielectric or some other insulating material disposed on a layer of conductive material) such that, e.g., the impedance between the electrical contact and the skin is substantially all reactive (that is, such that the impedance has a real or resistive component that is substantially zero). An electrical contact could include a surface texture configured to increase the effective surface area of the electrical contact.

In some examples, a detected impedance between an electrical contact and a skin surface or between two or more electrical contacts mounted to a skin surface could be detected and used to determine physiological parameters of the skin. For example, a moisture content, a Galvanic skin resistance, a degree of perfusion, an ionic content, a pressure and/or force between the skin and an electrical contact, or some other properties of the skin could be determined based on an impedance between two or more electrical contacts mounted to the skin.

In some examples, a quality or other property of the electrical connection between an electrical contact and skin and/or of the mounting of a device including an electrical contact to the skin could be determined or assessed based on an impedance detected as described herein. In examples wherein electrical contacts are used to detect biosignals (e.g., voltages and/or currents related to electrocardiograms, electromyograms, Galvanic skin potentials) from locations on a skin surface, a decrease in the impedance between the electrical contacts and the skin could allow for improved (e.g., lower noise, higher signal magnitude) detection of such biosignals. Additionally or alternatively, a detected impedance could be used as a proxy indication of the quality and/or stability of the mounting of a device to an external body surface. For example, the impedance between an electrical contact of a device and a skin surface could reduce over time is the device has been mounted securely to the skin surface.

Over time, moisture could accumulate between a portion of the skin surface and the electrical contact mounted thereto (e.g., related to secretion of sweat and/or emission of extracellular fluid or other fluids) decreasing the impedance. Increased moisture on or within the skin could increase the pliability or compliance of the skin, allowing it to more closely conform to the surface of an electrical contact. Relative motion and/or exerted pressure between the skin and the electrical contact could act to expel air trapped between the electrical contact and the skin. Over time, moisture from the skin could fully wet the surface of the electrical contact. Additional or alternative processes or factors to those described here could contribute to the reduction of the impedance between an electrical contact and an external body surface over time. Further, an electrical contact and/or a device including such being improperly mounted to (e.g., strapped to, adhered to, or otherwise maintained in secure contact with) a skin surface could result in an impedance between the electrical contact and the skin remaining at a high value.

Thus, a detected impedance could be used to determine how a device is mounted to a skin surface (e.g., to determine whether the device is correctly mounted to the skin surface such that one or more electrical contacts are in secure, consistent contact with respective locations on the skin). Such a device could operate to indicate such mounting information to a user, e.g., to use a display or other indicating means to provide an indication to a user that the device is properly or improperly mounted to skin. In some examples, a device could determine that a detected impedance is above a specified threshold (or otherwise determine, based on a detected impedance, that the device is improperly mounted to a wearer) and could responsively provide an indication to a user that the device is improperly mounted. The user could then re-mount the device (e.g., remove and reposition the device, reapply an adhesive, tighten a strap or other means for mounting the device to skin).

In some examples, a device could determine that a detected impedance is below a specified threshold (or otherwise determine, based on a detected impedance, that the device is properly mounted to a wearer and/or that an interface between the device and the skin is suitable to perform some measurement(s)) and could responsively provide an indication of such to a user. The user could then take some action related to the operation of the device, e.g., the user could begin to engage in exercise, to eat a meal, to take a medication, to receive a therapy, or to engage in some other activity related to the operation of the device (e.g., operation to detect one or more physiological parameters of the user while the user engages in the activity). In an example, the device could be mounted to a wrist of a user and could include two or more electrical contacts configured to mount to skin of the wrist of the user. The user could touch a further electrical contact of the device with a finger of an arm opposite the arm to which the device is mounted in response to receiving an indication from the device (e.g., an indication that a detected impedance between the two or more electrical contacts and the skin of the wrist is below some specified threshold). The device could then detect an electrocardiogram or some other biosignal between one or more of the electrical contacts mounted to the wrist and the further electrical contact being touched by the user's finger.

A device could additionally or alternatively perform some operation based on a detected impedance. For example, the device could operate, responsive to determining that a detected impedance between one or more electrical contacts of the device and a skin surface to which the device is mounted it less than some threshold, to detect a voltage between, current through, or some other electrical signal related to one or more of the electrical contacts (e.g., to detect a Galvanic skin potential, an electrocardiogram, an electromyogram). Further, a magnitude, spectral content, or some other properties of such a detected signal could be scaled, normalized, or otherwise modified based on a detected impedance (e.g., to correct for attenuation of the detected biosignal by electrical properties of the interface between one or more electrical contacts and skin of an external body surface) and/or a gain, filter cutoff frequency, amplitude of a current and/or voltage applied to the skin, or some other parameters of operation of components of the device could be specified based on a detected impedance.

Additionally or alternatively, the device could determine, based on a detected impedance, that the device is securely mounted to the skin surface and/or has been securely mounted for a specified period of time (e.g., based on a determination that a detected impedance is less than a threshold). The device could, responsive to such a determination, operate one or more sensors to detect a physiological parameter via the skin surface to which the device is mounted. This could include detecting one or more optical properties of the skin, e.g., by illuminating elements beneath the skin surface (e.g., blood within a portion of subsurface vasculature) and detecting light scattered by, reflected by, fluorescently re-emitted by, or otherwise emitted from the elements of the body via the skin surface. Such detected optical properties could be related to flow rate, volume, level of oxygenation, or other properties of blood in a portion of subsurface vasculature, the location, number, concentration, or other properties of fluorophores or other optical substances in the portion of subsurface vasculature and/or skin (e.g., fluorescent tags configured to bind to an analyte of interest, naturally occurring fluorophores in a cancer cell), or to some other physiological parameter of interest.

Various elements of a body (e.g., the heart) create electric fields within the body (e.g., during the process of pumping blood). The temporal and spatial properties of such fields are related to the sum of a plurality of ionic currents that flow within the elements (e.g., the heart, a muscle, a nerve) as a result of the depolarization and repolarization of electrically active cells of the body (e.g., cardiomyocytes, skeletal muscle fibers, axons of a nerve) during various activities of the body (e.g., during a heartbeat). These electric fields within the body can result in voltage fluctuations at the surface of the skin (and other locations within the body) being related at least in part to such electrical activities (e.g., with processes of the heart related to the pumping of blood during heartbeats). As a result, measurement of these voltage fluctuations could be used to detect and/or determine information about the activities of such elements of the body, e.g., to determine a health or medical state (e.g., a disease state) of the body (e.g., a disease state of the heart).

An electrocardiogram (ECG) or other biopotential waveform can be extracted from voltage fluctuations between two (or more) locations on the skin of a person (e.g., by using electrodes to grant a measurement device electrical access to the two or more skin locations). The magnitude, phase, sign, or other properties of such a signal can be related to the locations on the skin surface from which the signals are detected, e.g., related to a relative location of the skin locations and the elements of the body generating the electrical signals, the geometry of the body, the conductivity of tissues disposed between the skin locations and the elements of the body generating the electrical signals, or some other electrical, geometric, or other properties of the body. For example, ECG waveforms can be extracted from pairs of skin locations on a person, such as between the left and right arms, between the right arm and left leg, and between the left arm and left leg.

The sign, phase, waveform shape, or other properties of ECG waveforms detected in such a way can be related to the skin locations used to detect the ECG waveforms, e.g., the ECG waveform can be preferentially related to the activity of different areas of the heart (e.g., the left or right ventricles, the left or right atria) by detecting voltages between different locations on the skin, e.g., different locations over the chest. ECG waveforms can also be extracted from combinations of voltage fluctuations at more than two skin locations; for example, an ECG waveform could be generated based on the difference between the voltage at a first electrode (e.g., an electrode over the heart) and a mean of the voltages of a set of other electrodes (e.g., a mean over the voltages of electrodes at the right arm, left arm, and left leg). In some examples, a low-magnitude ECG waveform can be detected between two electrical contacts on the same arm of a person.

Further, an extracted ECG waveform corresponding to a particular heartbeat generally includes a number of temporal features corresponding to phases of the activity of the heart during the particular heartbeat. Specifically, such an extracted ECG waveform may include a P wave (corresponding to depolarization of the atria of the heart), QRS complex (corresponding to depolarization of the ventricles of the heart), and a T wave (corresponding to repolarization of the ventricles). Such an extracted ECG waveform may include additional features (e.g., a U wave) and/or lack features (e.g., the T wave) according to a medical state of a person, an anatomical or physiological property of the person, and/or the properties of the electrodes and/or measurement equipment used to extract the ECG waveform. One or more properties of the extracted ECG waveform (e.g., a Q-T interval, an R-R interval, a P-R interval, an S-T interval, a Q-T interval, an amplitude and/or polarity of a T-wave, and amplitude, polarity, or some other parameter(s) of some other aspect of the ECG waveform) could be determined and used to determine a medical and/or health state of the heart and/or of the person containing the heart (e.g., a metabolic rate, a degree of physical exertion, an elevated or depressed level of one or more electrolytes, coronary ischemia, heart attack, cardiac hypertrophy, the presence of certain drugs and/or toxins).

A wearable device could be configured to detect the impedance between an electrical contact and a skin surface and/or between two or more electrical contacts that are mounted to respective locations on the surface of the skin. Such a wearable device could be further configured to extract one or more ECG waveforms or other biopotential signals from skin of a wearer by measuring voltage fluctuations between two or more skin locations of the wearer. This could include accessing the voltage fluctuations at the two or more skin locations using one or more of the electrical contacts used to detect an impedance. The connection between such a device and one or more skin locations could include long flexible leads connecting between a particular skin location to the wearable device, which could be located at some other location on or near the body of the wearer (e.g., the wearable device could be connected to a belt worn by the wearer, and leads could run from the belt location to electrical contacts at two skin locations at the wrists of the wearer). Additionally or alternatively, two or more electrical contacts could be disposed on the wearable device and configured to contact respective two or more skin locations. The two or more skin locations could be proximate to each other (e.g., the wearable device could be mounted to a wrist of the wearer, and the two skin locations could be skin location on the wrist of the wearer). Alternatively, the two or more skin locations could be distant locations and the wearer could move skin locations of the wearer's body to contact electrical contacts of the wearable device (e.g., the wearer could touch an electrical contact of a wearable device that is mounted to a first arm of the wearer with a finger of a second arm of the wearer).

As an example, a wearable device could be configured to mount to a first wrist (e.g., the left wrist) of the wearer and to have first and second electrical contacts configured to contact a first skin location on the first wrist. The wearable device could further include a third electrical contact configured to be contacted by a second skin location of the wearer. That is, the wearer could move a portion of the wearer's body (e.g., a right hand) proximate to the wearable device such that a second skin location (e.g., a finger, hand, or wrist location of the arm of the wearer opposite the arm to which the wearable device is mounted) is in contact with the third electrical contact of the wearable device. In this way, the wearable device could enable periodic extraction of ECG waveforms from voltage fluctuations between the two skin locations (e.g., between a wrist location of the left arm and a finger location of the right arm). Such a wearable device could be configured in the form of a wristwatch or other wrist-mounted device (i.e., having a central housing (on or within which could be mounted first and/or second electrical contacts) mounted to the wrist by e.g., a strap or band configured to encircle the wrist) and could include means for performing additional functions, e.g., indicating a time and/or information about extracted ECG waveforms to the wearer.

FIG. 1A illustrates such an example wearable device 110 mounted to a wrist of a first arm 105a of a wearer 100 during a first period of time. The wearable device 110 includes a housing 120 mounted to the wrist of the first arm 105a by a mount 140 (e.g., a strap or band). The wearable device further includes first (not shown), second (not shown), and third 130 electrical contacts. The first and second electrical contacts are disposed on an inside (i.e., wrist-facing) side of the housing 120 and configured to contact skin at a first external body surface (i.e., skin of the wrist of the first arm 105a) when the housing 120 is mounted on the wrist of the first arm 105a. The third electrical contact 130 is configured to be contacted by skin of a second external body surface (e.g., by finger, hand, wrist, or other skin of a second arm 105b of the wearer 100). The wearable device 110 additionally includes electronics (e.g., a signal conditioner, not shown) electrically connected to the first, second, and third 130 electrical contacts and configured to detect an impedance between the first and second electrical contacts and to extract an ECG waveform (related to the electrical activity of the heart 101 of the wearer 100) from voltage fluctuations between the third 130 electrical contact and at least one of the first and second electrical contacts.

The wearable device 110 could operate, during the first period of time (illustrated in FIG. 1A), to detect the impedance between the first and second electrical contacts. The detected impedance could be related to how well the device 110 is mounted to the wrist (e.g., whether the device is securely mounted such that the device engages in minimal motion relative to the wrist, whether a skin-contacting surface of the device is in consistent contact with skin of the wrist). The device 110 could be configured to provide an indication related to the detected impedance, e.g., to instruct the wearer 100 to remove and re-mount the device 110, to adjust the location of the device 110 on the wrist (e.g., such that the first and second electrical contacts can develop a better electrical connection to skin of the wrist), to tighten the strap 140 of the device 110, or to otherwise improve the mounting of the device 110 to the wrist. Further, the device 110 could operate a sensor (e.g., an optical sensor) to detect a physiological parameter of the wearer 100 via the skin of the wrist in response to a determination, based on the detected impedance, that the device 110 is securely mounted to the wrist. The device 110 could also provide an indication to the wearer 110 responsive to determining, based on a detected impedance, that the device 110 is securely mounted to the wrist. For example, the wearer 100 could engage in exercise, take a medication, or engage in some other activity in response to such an indication and the device 110 could detect some physiological parameter related to such activities.

The detected impedance can also be related to how well the first and second electrical contacts are electrically connected to skin of the wrist. The device 110 could be configured to detect some biosignal (e.g., a Galvanic skin potential, an ECG between the first and second electrical contacts and/or between the third electrical contact and at least one of the first and second electrical contacts) in response to determining, based on the detected impedance, that the first and second electrical contacts have a stable, low-impedance electrical connection to skin of the wrist. This could include providing an indication, responsive to such a determination, to the wearer 100 to touch the third contact with skin (e.g., a finger) of the second arm 105b.

FIG. 1B illustrates the wearable device 110 and wearer 100 during a second period of time when the wearer 100 is positioning skin of a finger of the second arm 105b in contact with the third electrical contact 130. In this state, electronics (e.g., a signal conditioner) of the wearable device 110 could extract an ECG waveform related to the electrical activity of the wearer's 100 heart 101 during the second period of time from voltage fluctuations between the first and second 130 electrical contacts.

The wearer positioning skin of the finger (or some other location) of the second arm 105b proximate to the second electrical contact 130 could be performed a plurality of times to enable to extraction of ECG waveforms during a plurality of respective periods of time. The wearer positioning skin of the finger of the second arm 105b proximate to the second electrical contact 130 could be performed at the initiative of the wearer, e.g., in response to the wearer having performed and/or being about to perform a strenuous task (e.g., exercise), experiencing some symptoms (e.g., fatigue, nausea, vertigo, heart palpitations, orthostatic hypertension), having received and/or being about to receive a drug (e.g., having taken nitroglycerin). In some examples, the wearer could additionally operate the device to indicate some symptoms or other information related to an extracted ECG waveform. Additionally or alternatively, the wearer positioning skin of the finger of the second arm 105b proximate to the second electrical contact 130 could be performed in response to an indication (e.g., a vibration, a sound, a visual indication on a display of the device 100, an indication through some other device in communication with the wearable device 110) that the wearer should perform such an action to enable the extraction of an ECG waveform by the wearable device 110. For example, the wearer 100 could position the skin of the finger of the second arm 105b in contact with the third electrical contact 130 in response to receiving an indication from the device 110 that is related to a detected impedance between the first and second electrical contacts being less than a specified threshold.

FIG. 2 illustrates an electrical circuit 200 modeling elements of the wearer 100 and wearable device 110 of FIGS. 1A and 1B. The electrical circuit 200 includes a time-varying voltage source 201 corresponding to the time-varying electrical field generated by the heart 101 of the wearer 100. The electrical circuit 200 additionally includes elements corresponding to the wearable device 110 (illustrated by bounding box 210). These elements 210 include equivalent resistor/capacitor networks 240a, 240b, 230 corresponding to the electrical properties of the first, second, and third 130 electrical contacts and their electrical coupling to respective first and second skin locations. The elements of the wearable device 210 additionally include an impedance detector 250 electrically connected to the first 240a and second 240b electrical contacts and configured to detect an impedance between the first 240a and second 240b electrical contact (that is, through the first contact 240a via a first area of the skin surface, through the skin, and then through the second contact 240b via a second area of the skin surface). The wearable device 210 further includes an amplifier 220 electrically connected to the first 240a and third 230 electrical contacts and configured to extract an ECG waveform from voltage fluctuations between the first 240a and third 230 electrical contacts.

Inputs of the amplifier 220 have finite input impedances. Thus, an ECG signal detected by the amplifier 220 can be attenuated, filtered, phase-shifted, or otherwise modified relative to a corresponding time-varying voltage between areas of skin contacted by the first 240a and third 230 electrical contacts, respectively, by an amount related to a ratio or other relationship between the input resistances of the amplifier 220 (e.g., between approximately a megaohm and approximately a gigaohm) and the impedances between the first 240a and third 230 electrical contacts and respective locations on the skin. The electrical circuit 200 further includes resistors 205a, 205b, 205c, 207a representing the electrical properties (e.g., resistance to current flow) of the arms 105a, 105b and other tissue (e.g., chest tissue) between the heart 101 and the first, second, and third 130 electrical contacts. A switch 207b represents the control-able electrical contact between the third electrical contact 130 and skin of the second arm 105b. Thus, the switch 207b is open to model the electrical behavior of the wearer 100 and wearable device 110 during the first period of time (corresponding to the scenario illustrated by FIG. 1A) and closed to model the electrical behavior of the wearer 100 and wearable device 110 during the second period of time (corresponding to the scenario illustrated by FIG. 1B).

Thus, an ECG waveform extracted when the wearer 100 positions skin of the finger (or some other location) of the second arm 105b proximate to the third electrical contact 130 could correspond to a lead I ECG recording. That is, in embodiments wherein the wearable device 110 is mounted to a right wrist location and the amplifier 220 extracts an ECG waveform by sensing the voltage fluctuations of the first electrical contact relative to the second electrical contact, the extracted ECG waveform corresponds to a lead I ECG recording. Alternatively, the wearable device 110 could be mounted to a left wrist location, and the extracted ECG waveform could correspond to an inverted lead I ECG recording. The user could indicate to the wearable device 110 (e.g., using a user interface of the wearable device 110) that the wearable device is mounted to a left (or right) wrist location. Additionally or alternatively, the wearable device 110 could determine that it is mounted to a left (or right) wrist location based on features (e.g., the polarity of the QRS complex) of an extracted ECG waveform.

Note that the illustrated resistances are a simplified representation of equivalent electrical circuits between the heart and skin locations contacting the first, second, and third 130 electrical contacts. For example, the circuit 200 could be expanded to provide additional resistances representing the flow of current from the heart to the first and second electrical contacts. Such an expanded circuit could be used to model voltage differences between the areas of the skin connected to the first and second electrical contacts. Such an expanded circuit could provide a model for the detection of an ECG signal by detecting voltage differences between the first and second electrical contacts (e.g., by connecting the amplifier 220 inputs to the first 240a and second 240b electrical contacts). The magnitude of such a detected ECG signal would be reduced, given a particular voltage waveform output by the time-varying voltage source 201, relative to an ECG signal detected between the third Parameters of the electrical circuit 200 are related to electrical properties of the body of the wearer 100, of the first, second, and third 130 electrical contacts, and to properties of the interface between the first, second, and third 130 electrical contacts and respective areas of skin. Thus, the parameters of the electrical circuit 200 could be related to a dryness of other state of the skin locations, a type of skin at the skin locations, a degree of force applied between the skin locations and respective electrical contacts, or other considerations. Such parameters could vary over time related, e.g., to the accumulation of moisture between such contacts and the skin, wetting of surface of the electrical contacts by such moisture, the skin conforming more closely with the surface of the electrical contacts, or some other factors or processes. For example, the impedance between the first and second contacts and the skin of the wrist of the first arm 105a could, when the device 110 is correctly and stably mounted to the wrist, decrease over time.

Further, the parameters of the electrical circuit 200 could be related to the composition and configuration of the electrical contacts (e.g., a composition of a surface of the electrical contacts, a texture of the surface of the electrical contacts, a geometry of the electrical contacts). Correspondingly, one or more properties (e.g., an input impedance, a frequency response, a bandwidth, a sensitivity, a maximum input amplitude) of the amplifier 220 could be specified and/or controlled relative to expected values of those properties of the body of the wearer 100, of the first, second, and third 130 electrical contacts, and/or of the interface between the first, second, and third 130 electrical contacts and respective areas of the skin (e.g., to allow the extraction of low-noise, high-amplitude, or otherwise optimized ECG waveforms). Further, the amplifier 220 or other elements of the device 210 could be operated based on impedances detected using the impedance detector 250. For example, the amplifier 220 could be operated to extract ECG signals when an impedance detected using the impedance detector 250 is below a specified threshold (e.g., a threshold specified relative to an input impedance of the amplifier 220).

Electrical contacts of the wearable device 110 could be configured in a variety of ways to allow the extraction of an ECG waveform from voltage fluctuations between the electrical contacts under a range of physiological and environmental conditions. The electrical contacts could have a variety of surface compositions to allow ohmic (i.e., related to conduction by ionic and/or redox reaction across the surface of the electrical contacts) and/or capacitive (i.e., related to the accumulation of opposite charges on opposite sides of a surface of the electrical contacts) electrical coupling between the electrodes and skin locations of a wearer. Such surface compositions could include stainless steel, gold, platinum, silver, silver/silver-chloride, polymers or rubbers containing conductive particles, or other conductive or partially conductive materials. Further, the shape and/or surface texture of the electrical contacts could be specified to control one or more properties of the electrical interface of the electrical contacts with skin. For example, the electrical contacts could have a specified large area in contact with skin, could protrude from a housing toward the skin (e.g., could have a rounded and/or pointed protruding geometry), could have a surface texture (e.g., to increase an effective surface area between a conductor of the electrical contact and fluids on the surface of the skin), or could be configured in some other way.

In some examples, the electrical contacts could be configured to have a substantially capacitive electrical contact with skin; that is, an electrical contact could engage in substantially no direct ionic and/or redox conduction across the interface between the electrical contact and the skin. Conduction of currents between such an electrode and the skin could instead consist substantially of the accumulation of opposite charges on respective opposite sides of a substantially nonconductive barrier (e.g., a layer of dielectric material) between a conductor of the electrical contact and the skin. For example, an electrical contact could include a flat conductor having a substantially nonconductive dielectric coating configured to be in contact with skin. Additionally or alternatively, an electrical contact could have a textured conductive surface coated in a conformal layer of substantially nonconductive material. Other compositions and configurations of electrodes are anticipated.

An amplifier 220, impedance detector 250, or other electronics of the wearable device 110 could include a variety of components configured in a variety of ways to allow one or more ECG waveforms and/or impedance values detected using the first, second, and third 130 electrical contacts when the electrical contacts are contacting appropriate respective skin locations of the wearer 100 and/or to allow other operations and applications. The electronics could include analog and/or digital electronic components to enable analog and/or digital manipulations of electrical signals related to voltage fluctuations between the electrical contacts. Generally, the electronics include components configured to amplify and filter voltage fluctuations between the electrical contacts (e.g., one or more amplifiers, buffers, filters, operational amplifiers, resistors, capacitors, inductors, transistors, rectifiers, or some other linear or nonlinear electronic component or combinations thereof). The electronics can further include elements (capacitors, current sources, voltage sources, electronic switches) configured to inject a current though and/or apply a voltage across two or more of the electrical contacts (e.g., the first and second electrical contacts) to allow an impedance between such electrical contacts to be detected.

For example, the electronics could be configured to generate an electronic signal (e.g., to generate an extracted ECG waveform) that is related to a band-passed version of the voltage fluctuations between two or more electrical contacts. This could include applying the voltage fluctuations to a band-pass filter having a pass-band between approximately 0.05 Hertz and approximately 150 Hertz. Additionally or alternatively, an electronic signal could be digitally sampled and some digital filtering could be performed (e.g., by a processor of the wearable device 110) to generate an extracted ECG waveform. The electronics could include fast recovery circuitry configured to determine that one or more elements (e.g., amplifiers, filters) of the electronics are saturated and to responsively control one or more properties of the electronics (e.g., operate an electronic switch to discharge a capacitor, change a corner frequency or other parameter of a filter) to reduce the electronic saturation of the one or more elements of the electronics. Other configurations and applications of electronics of the wearable device 110 are anticipated.

The wearable device 110 and uses thereof illustrated in FIGS. 1A and 1B are illustrative examples; a wearable device as described herein could be configured in a variety of ways. Generally, such a wearable device could include at least two electrical contacts disposed on or toward an inside surface of the wearable device (e.g., on an inside surface of a housing, strap, or other element of the wearable device) such that the at least two electrical contacts are in contact with a first external body surface at a first skin location to which the wearable device is mounted. Generally, such a wearable device could also include at least one electrical contact disposed on or toward an outside surface (i.e., an outside contact) of the wearable device (e.g., on an outside surface of a housing, strap, or other element of the wearable device) such that the at least one electrical contact is not in contact with an external body surface at the first skin location to which the wearable device is mounted. The wearable device could be further configured to prevent electrical contact between the outside contact and an external body surface at the first skin location to which the wearable device is mounted, e.g., by increasing a distance between the outside contact and the external body surface, by disposing the outside contact on an outside surface of the wearable device far from an edge of the outside surface, by providing a nonconductive barrier between the outside contact and the external body surface, or operating or configuring the wearable device in some other way.

A wearable device (e.g., 110) could include additional sensors. For example, the wearable device could include accelerometers, optical pulse sensors, photoplethysmographic sensors, pulse oximeters, thermometers, acoustical sensors, force sensors, electric field sensors, magnetic field sensors, or some other sensor(s) configured to detect one or more properties of a wearer of the wearable device and/or of the environment of the wearable device. In some examples, information from different sensors of the wearable device could be combined to determine one or more physiological parameters of the wearer (e.g., to determine a health or medical state of the wearer). In some examples, such sensors could be operated based on an impedance detected by the device between two or more electrical contacts of the device. Such a detected impedance could be related to how securely the device is mounted to a skin surface of a body. In such examples, the detected impedance could be used to determine whether the device is securely mounted to the body (e.g., by determining whether the detected impedance is below a threshold) and the sensor(s) could be operated to detect physiological parameter(s) of the body responsive to a determining, based on the detected impedance, that the device is securely mounted to the body.

In some examples, a wearable device could be configured to extract an ECG waveform from voltage fluctuations between two or more skin locations of a wearer. The wearable device could be further configured to detect a volume of blood in a portion of subsurface vasculature of the wearer at a plurality of points in time (e.g., by illuminating the portion of subsurface vasculature and detecting light responsively received from the portion of subsurface vasculature, i.e., via photoplethysmography) to generate a waveform of the volume of blood in the portion of subsurface vasculature over time. Time differences or other comparisons of features of the extracted ECG waveform and the determined volume waveform (e.g., a time difference between a maximum of the volume waveform and a corresponding QRS complex of the ECG waveform) could be used to determine a flow rate, a pressure wave speed and/or latency, or other information about the blood in the portion of subsurface vasculature and/or information about the heart and vasculature of the wearer. Further, such determined information could be used to determine a health or medical state of the wearer, e.g., to determine a blood pressure of the wearer, to determine a degree of atherosclerosis of the vasculature of the wearer, etc.

Figure 3:
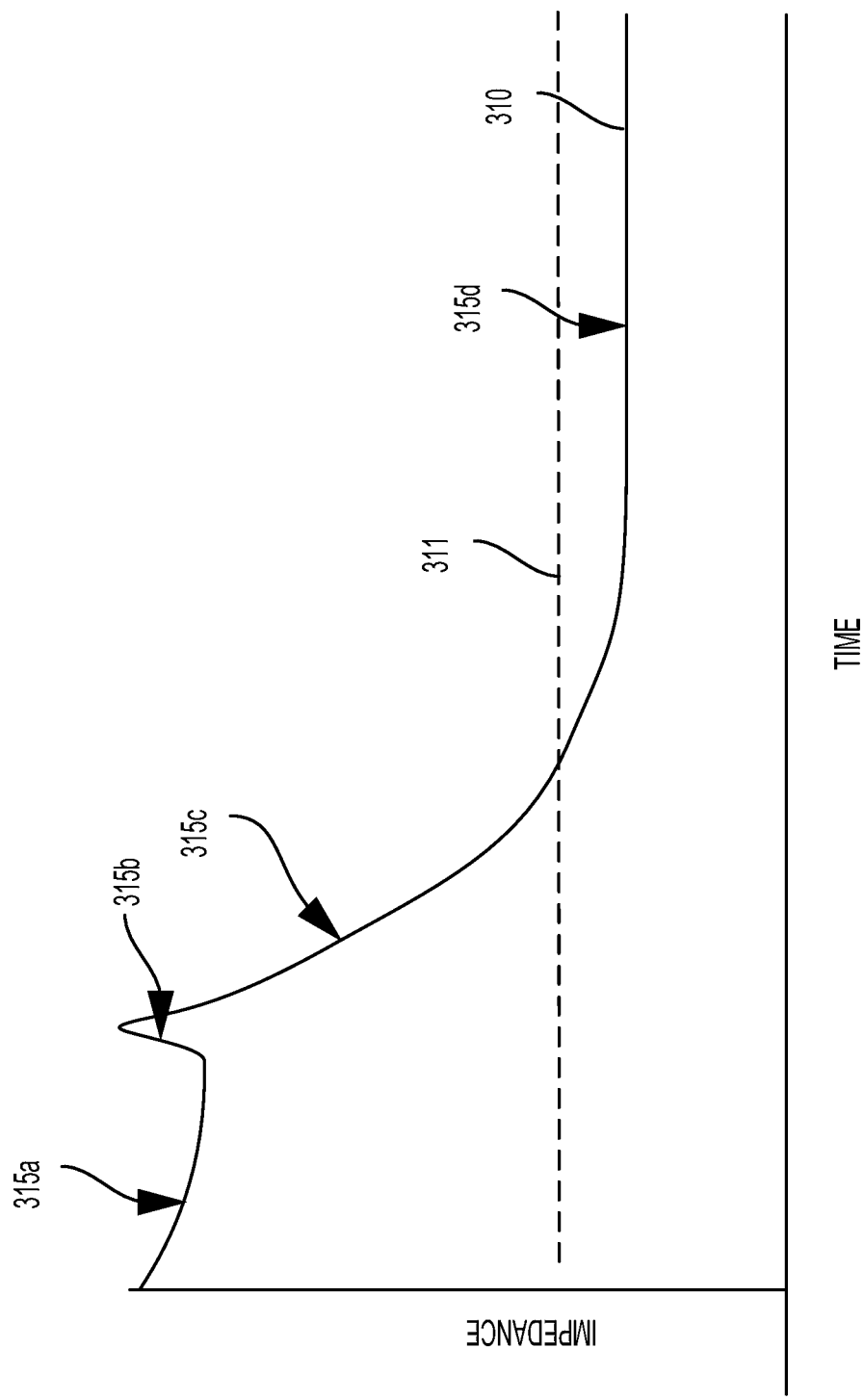
FIG. 3 shows the impedance between electrical contacts of a device over time.

As described elsewhere herein, an impedance between two electrical contacts of a wearable device that are mounted to a skin surface of a body can be related to the quality and/or stability of the mounting of the wearable device to the skin surface. This impedance can decrease over time, e.g., related to deposition of moisture (e.g., sweat) between the skin surface and the electrical contacts of the device. The impedance could be affected by relative motion of the device and the skin surface, deformation of the skin surface related, e.g., to motion and/or muscle activity of a wearer. FIG. 3A shows an example detected impedance 310 between electrical contacts of such a wearable device (e.g., 110) over time.

A first period 315a of the detected impedance 310 corresponds to a first period of time during which the device is improperly mounted to the skin. This could include the device being loosely strapped or otherwise pressed against the skin, electrical contacts of the device being in incomplete contact with skin, or some other factors or considerations. As shown, the impedance during the first period of time 315a decreases (e.g., due to accumulation of moisture between the device and the skin) but remains at a high level.

The second time period 315b of the detected impedance 310 corresponds to a second period of time during which the device is re-positioned, the device is removed and re-mounted, a strap or other mount of the device is tightened, or the mounting of the device to skin is otherwise changed. During the second period of time 315b, the detected impedance 310 increases due, e.g., to the removal of the device from the skin, a reduction in the pressure applied by electrical contacts of the device and the skin, a reduction in an area of contact between electrical contacts of the device and the skin, a loss of moisture disposed between the electrical contacts and the skin (e.g., due to exposure to the atmosphere), or some other factors or processes.

A third period 315c of the detected impedance 310 corresponds to a third period of time, subsequent to the second period of time, during which the device is properly mounted to the skin. This could include the device being firmly strapped or otherwise pressed against the skin, electrical contacts of the device being in full contact with skin, or some other factors or considerations. As shown, the impedance during the third period of time 315c decreases (e.g., due to accumulation of moisture between the device and the skin) toward a stable, low level, indicated by a fourth period 315d of the detected impedance 310 during a fourth period of time.

As described elsewhere herein, a device could operate to provide indications related to the detected impedance 310. For example, a wearer could change the mounting of the device (e.g., could remove and re-mount the device, could tighten a strap of the device) during the second period of time in response to an indication provided by the device. Such an indication could be provided responsive to a determination, during the first period of time, that the detected impedance 310 is above a specified threshold (e.g., specified threshold 311, illustrated in FIG. 3 as a horizontal dashed line) or according to some other determination. Additionally or alternatively, a wearer could engage in exercise, touch an electrical contact of the device to facilitate a measurement by the device (e.g., of an electrocardiogram), take a medication, or engage in some other activity during the third and/or fourth periods of time in response to an indication provided by the device. Such an indication could be provided responsive to a determination, during the third or fourth periods of time, that the detected impedance 310 is below a specified threshold (e.g., 311), that the detected impedance 310 has stabilized at a value below a specified threshold, or according to some other determination. The device could detect a physiological parameter, begin logging a physiological parameter over time, or perform some other operations responsive to a determination based on the detected impedance 310 (e.g., could begin detecting and recording a physiological parameter during the fourth period of time responsive to determining that the detected impedance 310 is below a specified threshold and/or that the detected impedance 310 has reached a stable value).

A device as described herein could make a variety of determinations based on an impedance between electrical contacts in contact with skin (or other tissue), or an impedance between an electrical contact and skin (or other tissue), detected at one or more points in time. Such determinations could include comparing an impedance (e.g., comparing the value of a real component, a resistive component, an imaginary component, a capacitive component, an inductive component, a reactive component, a magnitude, a phase angle or lag, one of the preceding properties at a particular frequency or across a range of frequencies, a linear or other combination of one or more of the preceding properties) detected at a particular point in time to a specified threshold. This could include determining that the detected impedance is less than the threshold, greater than the threshold, greater than a first threshold and less than a second threshold that is greater than the first threshold, or some other determination based on a comparison between the detected impedance and one or more specified thresholds.

In some examples, a threshold could be specified relative to a property of a wearable device. For example, a threshold could be specified as a fraction of an input impedance of an amplifier. In some examples, the threshold could be specified based on a previously detected impedance or some other consideration. For example, first impedance could be detected at a first point in time and used to determine a threshold (e.g., by determining a fraction of the first impedance). A second impedance could be detected at a second point in time and compared to the first impedance. The device could then operate (e.g., to detect an electrocardiogram or other physiological parameter or waveform, to provide an indication to a user) based on the comparison. A specified threshold could be determined based on a plurality of detected impedances and/or on a change in a detected impedance over time. For example, a device could detect a level and a rate of change of an impedance during a first period of time and could determine a specified threshold based on such information, e.g., based on an expected long-term stable value of the impedance (e.g., an expected value of the detected impedance 310 during the fourth period of time determined based on one or more values of the detected impedance 310 detected during the third period of time).

Devices as described herein could detect an impedance between two electrical contacts mounted to skin (or to some other tissue or tissue surface) in a variety of ways. This could include applying a specified voltage and/or current between/ through the electrical contacts and an amplitude, time dependence, or other properties of a current/voltage responsively developed through/between the electrical contacts could be detected and used to determine the impedance. The applied specified voltage and/or current could have a specified waveform or other property of variation over time, e.g., a specified frequency, pulse width, pulse repetition frequency, pulse rise time, or other properties. For example, an oscillating voltage at a specified frequency could be applied between two electrical contacts and an amplitude, relative phase, or some other property of a time-varying current responsively passing through the electrical contacts could be detected and used to determine an impedance (e.g., a magnitude, a phase, a real component, and imaginary component) between the two electrical contacts at the specified frequency. Additionally or alternatively, the applied voltage and/or current could be substantially constant (e.g., a DC voltage or current) during a specified period of time to provide for the detection of a DC impedance between the two electrical contacts.

In a particular example, a capacitor could be electrically connected between the two electrical contacts. The capacitor could be charged (e.g., charged to a specified voltage) during a first period of time and subsequently discharged through the two electrical contacts (e.g., through skin to which the electrical contacts are mounted). A voltage across and/or a current through the capacitor could be measured during the discharge to determine an impedance (e.g., a DC impedance, a phase and magnitude of an AC impedance at one or more frequencies, an impedance spectrum, a resistive, capacitive, inductive, and/or reactive component of the impedance) between the two electrical contacts.

Figure 4:
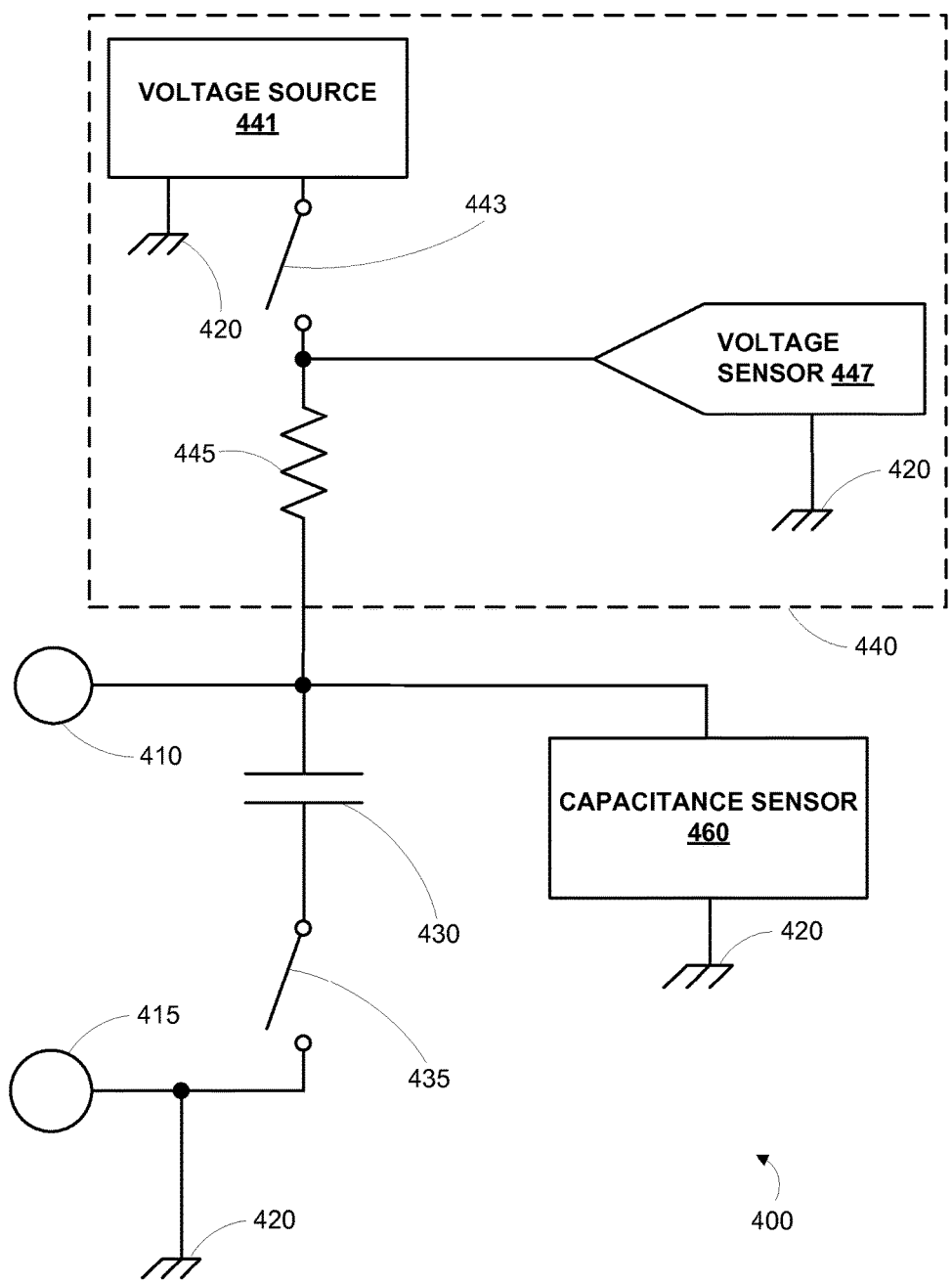
FIG. 4 is a functional block diagram of components disposed in an example wearable device.

FIG. 4 is a simplified circuit diagram of electronics 400 that could be disposed in a wearable device to measure an impedance between a first electrical contact 410 and a second electrical contact 415 disposed in the wearable device. Electronics 400 are configured to include a common electrical ground 420 electrically connected to the second electrical contact 415. The electronics include a capacitor 430 (having a capacitance, e.g., of approximately 0.01 microfarads) connected in series with an electronic switch 435; the series combination of the capacitor 430 and the electronic switch 435 is electrically connected between the first 410 and second 420 electrical contacts. The electronics 400 include an impedance detector 440 configured to obtain a measurement relating to the impedance between the first and second electrical contacts 410, 415 when the electronic switch 435 is closed. Impedance detector 440 can include a voltage source 441, a voltage source switch 443, a current-limiting resistor 445 (having a resistance, e.g., of approximately 1 ohm), and a voltage sensor 447. The impedance detector 440 and/or elements thereof could additionally be used to detect a voltage between the electrical contacts 410, 415 (e.g., a voltage related to an electrocardiogram or other biosignal), e.g., by operating the voltage sensor 447 to detect a voltage while the switches 435, 553 are open. The electronics 400 also include a capacitance sensor 460 configured to measure a capacitance between the first and second electrical contacts 410, 415 (e.g., when the electronic switch 435 is open).

In the example of FIG. 4, the voltage source 441 is electrically connected to the first electrical contact 410 through the voltage source switch 443 and the resistor 435. Additionally, the voltage sensor 447 has an input electrically connected to the first electrical contact 410 through the resistor 445. Further, at least the reference voltage source 441, voltage sensor 447, capacitance sensor 460, and electronic switch 435 are electrically connected to the common electrical ground 420 that is electrically connected to the second electrical contact 415.

Figure 8:
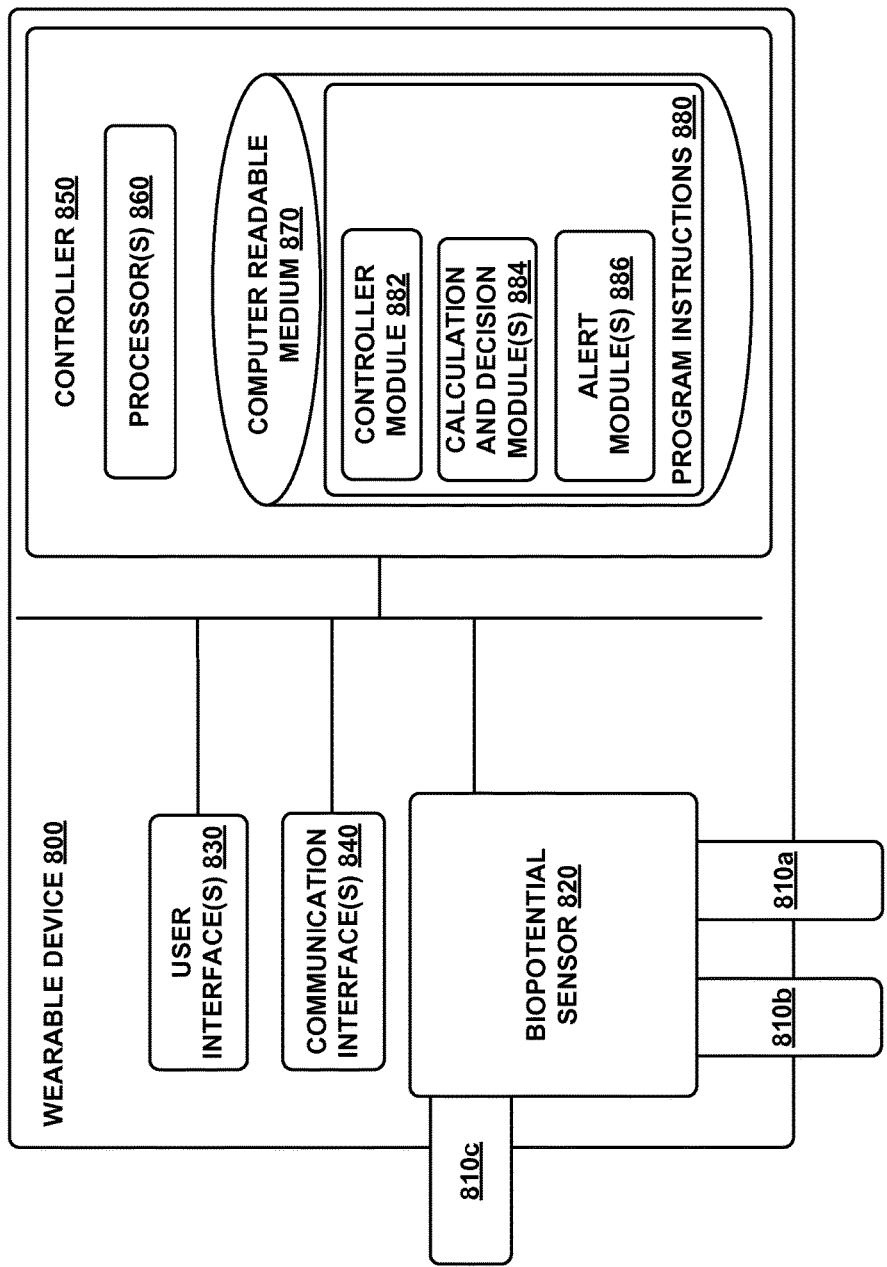
FIG. 8 is a functional block diagram of components disposed in an example wearable device.

Electronics 400 could be disposed in a wearable device (e.g., the wearable devices 100, 500, 800 illustrated in FIGS. 1, 5, and 8). Individual elements of the electronics 400 could be embodied as respective discrete components. Additionally or alternatively, one or more elements of the electronics 400 could be incorporated into one or more integrated circuits. In examples where the electronics 400 are included in a wearable device composed of multiple housings or other subassemblies, the elements of the electronics 400 could all be disposed in a single housing or subassembly or elements of the electronics 400 could be disposed in multiple housings or subassemblies and connected using wires, cables, or other means passing between housings or subassemblies.

Obtaining a measurement relating to the impedance between the first and second electrical contacts 410, 415 can include operating the impedance detector 440 to charge the capacitor 430 (e.g., to a specified voltage, during a specified duration of time, using a specified current, using a specified voltage, or according to some other specified operation) during a first period of time when the electronic switch 435 is closed. This could include closing the voltage source switch 443 during the first period of time such that the voltage source 441 charges the capacitor 430 via the resistor 445 at a rate (i.e., with a current) related to at least the capacitance of the capacitor 430, the resistance of the resistor 445, and a difference between the voltage provided by the voltage source 441 and the voltage across the capacitor 430. The impedance detector 440 could then be operated to detect a voltage across the capacitor 430 at one or more points in time as the capacitor discharges through the skin at an external body surface via the first and second electrical contacts 410, 415 during a second period of time when the electronic switch 435 is closed.

This could include opening the voltage source switch 443 during the second period of time such that the capacitor 430 discharges through the electrical contacts 410, 415. One or more properties (e.g., a decay rate, a decay profile, a decay time to half-voltage) of the voltage across the capacitor can be related to one or more properties (e.g., a resistive component, a reactive component, a magnitude, a spectrum) of the impedance between the first and second electrical contacts 410, 415. The one or more properties could be detected using the impedance detector 440 (e.g., by using an ADC of the voltage sensor 447 to measure the voltage related to the voltage across the capacitor at one or more points in time, by detecting the output of a comparator and/or Schmitt trigger of the voltage sensor 447 that receives the voltage across the capacitor as an input) to determine the impedance between the first and second electrical contacts 410, 415. Further, the specified capacitance of the capacitor could be chosen to allow accurate measurement of the impedance when mounted to skin (e.g., by having a value chosen based on an expected impedance between the first and second electrical contacts 410, 415). For example, the capacitance of the capacitor could be approximately 0.01 microfarads.

The voltage sensor 447 could be part of a microcontroller disposed in a wearable device. The voltage sensor 447 could be configured as a discrete component disposed in a wearable device. The voltage sensor 447 could be operated by a microcontroller or other processor(s) to make a measurement of a voltage related to the voltage between the first and second electrical contacts 410, 415. The voltage sensor 447 could include one or more comparators, Schmitt triggers, direct-conversion ADCs, successive-approximation ADCs, sigma-delta ADCs, or some other type(s) of ADC. The voltage sensor 447 could include an amplifier, a filter, a sample-and-hold, and/or some other components.

In some examples, the voltage source 441, voltage sensor 447, voltage source switch 443, and/or other elements of the impedance detector 440 could be elements of a microprocessor that are electronically coupled to a pin of the microprocessor (e.g., logic gates, capacitors, high-impedance electrical switches (e.g., CMOS FETs), or other microelectronics) that is coupled to the capacitor 430 and the first electrical contact 410 via the resistor 445 or via some other electronic component(s). For example, the voltage source 441 could be an internal voltage supply of the microprocessor, and the voltage source switch 443 could be a gate of the microprocessor configured to electrically connect the internal voltage supply and/or an internal ground of the microprocessor (e.g., an internal ground electrically connected to the common electrical ground 420) to a pin of the microprocessor and to appear as a high impedance element when not connecting the pin to the internal voltage supply and/or the internal ground (e.g., to provide a 'three-state' digital output to the pin). An ADC of the microprocessor could additionally be configured to electrically connect to the pin and to act as the voltage sensor 447.

The voltage sensor 447 could be used to measure a voltage relating to an impedance between the electrical contacts 410, 415. The voltage sensor 447 could also be used to detect other signals. In some examples, the voltage sensor 447 could be used to detect whether the electrical contacts 410, 415 are in contact with skin proximate to the electrical contacts 410, 415. The voltage sensor 447 could be used to detect a biosignal (e.g., an electrocardiogram, an electromyogram, a Galvanic skin potential) via the electrical contacts 410, 425. The voltage sensor could be used to detect when an external charger or other power source is connected to the first and second electrical contacts 410, 415 and/or a charge state of a rechargeable battery connected to the electronics 400. Other uses of the voltage sensor 447 are anticipated.

The impedance detector 440 could include additional and/or alternate circuitry than that disclosed above. The impedance detector 440 could include linear and nonlinear filtering circuitry and/or voltage isolation circuitry. For example, the impedance detector 440 could include clamping diodes, blocking resistors, blocking capacitors, electronic switches, or other elements configured to prevent components of the impedance detector 440 from being damaged by voltages and/or currents at/through the electrical contacts 410, 415. The impedance detector 440 could include one or more analog components or functional blocks. The impedance detector 440 could include analog electronics to perform some analog calculation and/or filtering based on a measured voltage or other signal; the results of this analog calculation and/or filtering could be used to perform some function or could be digitized for use by a processor or microcontroller.

The voltage source 441 could be any component configured to provide a stable, specified voltage relative to a common electrical ground 420. For example, the voltage source 441 could include a forward or reverse biased Zener diode, germanium diode, silicon diode, and/or avalanche diode. The voltage source 441 could additionally or alternatively include a bandgap voltage reference. The voltage source 441 could be temperature stabilized. In some examples, a voltage provided by the voltage source could be adjustable, for example by a microcontroller connected to the reference voltage source. The voltage source 441 could be an internal voltage provided by a microcontroller.

The resistor 445 could be any electronic component having a stable reference resistance value. For example, the resistor could be a thin-film resistor, a thick-film resistor, a laser-trimmed resistor, a wire-wound resistor, or some other type of resistive element. The resistor 445 could be an element of a microcontroller. In some examples, the resistor 445 could have an adjustable resistance, and the adjustable resistance could be controlled by e.g. a microcontroller. In some examples, the resistor 445 could have a resistance of approximately 1 ohm, e.g., to limit an amount of current supplied by the voltage source 441 to charge the capacitor 430.

The electronic switch 435 and voltage source switch 443 could be any component that can be operated to allow substantially no current to flow through itself during a first period of time and to allow current to flow substantially unimpeded (i.e., to have a very low resistance) during a second period of time. The switches 435, 443 could include a FET, a MOSFET, a BJT, an IGBT, or some other switchable electronic component. The switches 435, 443 could be configured to contact a heat sink or other heat management component to reduce the temperature of the switches 435, 443 during operation. The switches 435, 443 could be configured (e.g., could have a wide and/or or deep channel, gate, or other semiconductor feature) to have a very low 'on'-resistance (e.g., on the order of milli-ohms), a very low gate capacitance, or some other specified properties according to an application.

The electronics 400 include a capacitance sensor 460 configured to obtain a measurement relating to the capacitance between the first and second electrical contacts 410, 415 (e.g., a capacitance of skin between the contacts 410, 415) when the electronic switch 435 is open. The capacitance sensor 460 could be configured to apply specified currents and/or voltages to the first and second electrical contacts 410, 415 via a variety of electronic components in order to measure the capacitance. For example, the capacitance sensor 460 could include a relaxation oscillator. That is, the capacitance sensor could include components configured to repeatedly charge and discharge an equivalent capacitance between the first and second electrical contacts 410, 415 (e.g., a capacitance of skin, air, or other substances between the first and second electrical contacts 410, 415) in a specified manner (e.g., by applying a specified charge/discharge current, by apply a specified charge/discharge voltage to the first and second electrical contacts 410, 415 via a resistor having a specified resistance) such that a frequency, a duty cycle, or some other property of the operation of the relaxation oscillator is related to the capacitance between the first and second electrical contacts 410, 415.

III. Example Wearable Devices

Wearable devices as described herein could be configured in a variety of ways. In some examples, a wearable device could be configured to be mounted to a wrist location of a first arm of the wearer. Further, such a wearable device could include first and second electrical contacts disposed on a housing (e.g., on an inside surface of the housing) of the wearable device and configured to contact skin at wrist location when the wearable device is mounted on the wrist location. Such a wearable device could detect and impedance between the first and second electrical contacts, e.g., to determine whether the device is mounted to skin, to determine whether the device is securely and/or stably mounted to the skin, to determine an impedance between the first and second electrical contacts and the skin, or according to some other application.

Such a wearable device could additionally include a third electrical contact (e.g., disposed on an outside surface of the wearable device) configured to be contacted by skin of a second body surface on a second arm of the wearer such that electronics (e.g., a signal conditioner) of the wearable device could extract an electrocardiogram signal from voltage fluctuations between the third electrical contact and at least one of the first and second electrical contacts when the third electrical contact is contacted by skin of the second body surface and the wearable device is mounted to the wrist location. Additionally or alternatively, an electrocardiogram signal could be detected based on detected voltages between the first and second electrical contacts. Further, an impedance could be detected between the third electrical contact and at least one of the first and second electrical contacts. Other operations and/or configurations of a wearable device as described herein are anticipated.

Figure 5A:
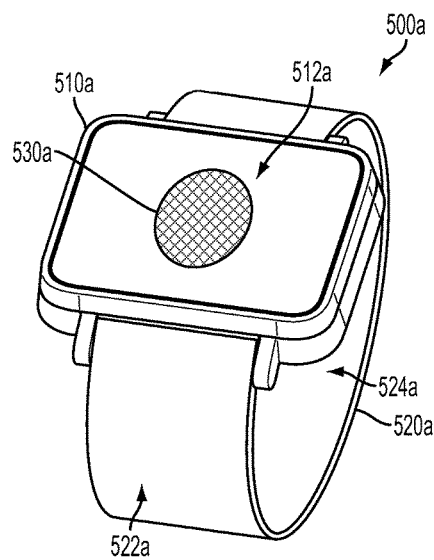
FIG. 5A is a perspective view of an example wearable device.

As an example, FIG. 5A illustrates a wearable device 500a similar to the wearable device 110 illustrated in FIGS. 1A and 1B. The wearable device 500a can be configured to extract an electrocardiogram or some other biosignal from voltage fluctuations between skin at first and second external body surfaces. The term "wearable device," as used in this disclosure, refers to any device that is capable of being worn at, on or in proximity to an external body surface, such as a wrist, ankle, waist, chest, or other body part. A mount 520a, such as a belt, wristband, ankle band, etc. can be provided to mount the device at, on or in proximity to the external body surface. In some embodiments, a mount could additionally or alternatively include an adhesive. For example, a mount could include and adhesive and could be configured such that it could be used to mount a wearable device to an external body surface of a wearer without wrapping around a part of the wearer (e.g., a limb). The mount 520a may prevent the wearable device 500a from moving relative to the body to ensure consistent contact between an electrical contact or other sensor of the wearable device 500a and the skin to enable consistent extraction of an electrocardiogram and/or measurement of some other property of the wearer. In one example, shown in FIG. 5, the mount 520a takes the form of a strap or band that can be worn around a part of the body.

A housing 510a is disposed on the mount 520a such that the housing 510a can be positioned on a first external surface of a first arm of the body (e.g., a surface of a wrist of the body). The housing 510a has an outside surface 512a that is away from the first external surface of the body and an inside surface (not shown) that is toward and/or in contact with the first external surface of the body when the housing 510a is positioned on the first external surface of the body. Similarly, the mount 520a has an inside surface 524a and an outside surface 522a. A third electrical contact 530a is disposed in the middle of the outside surface 512a of the housing 510a and configured to be contacted by skin of a second external body surface of a second arm of the body (i.e., an arm opposite an arm to which the wearable device 500a is mounted). Operated and/or mounted in this way, first and second electrical contacts (not shown) disposed on the inside surface of the housing 510a could contact skin at the first external surface of the body such that an electrocardiogram or other biosignal (as measured between the first and second external body surfaces, e.g., between a wrist of a first arm and a finger of a second, opposite, arm) could be extracted from voltage fluctuations between the third 530a electrical contact and at least one of the first and second electrical contacts. Further, an impedance between the first and second electrical contacts could be detected and used, e.g., to time the detection of a biosignal using two or more of the electrical contacts, to determine whether the device 500a is securely mounted to a skin surface, or to provide some other application.

The first, second, and third 530a electrical contacts could be composed of an electrically conductive material, such as a metal or a combination of metals, or a nonmetal conductor. The first, second, and third 530a electrical contacts could be composed of the same material or different materials. The first, second, and third 530a electrical contacts could each be composed of a single material or could be composed of multiple materials. For example, the electrical contacts could have a bulk composed of a first material and a surface plating of another material. For example, the electrical contacts could have a bulk composed of copper and a surface composed of gold or of gold alloyed with nickel and/or cobalt. Alternatively, the surface layer could be composed of stainless steel, gold, platinum, silver, silver/silver-chloride, polymers or rubbers containing conductive particles, or other conductive or partially conductive materials. The surface layer could be deposited by a number of methods familiar to one skilled in the art; for example, electroplating. Other compositions are possible, as well. Additionally or alternatively, the electrical contacts could be configured to be substantially capacitively coupled to respective external body surfaces by, e.g., including a flat conductor having a substantially nonconductive dielectric coating configured to be in contact with skin. Other compositions and configurations of electrodes are anticipated. Further, protruding aspects of the electrical contacts could have an inscribed, cast, and/or pressed texture or pattern. Additionally or alternatively, the exposed aspects of the electrical contacts could be roughened mechanically, chemically, or by some other method.

One or more of the electrical contacts could be spring loaded. That is, the electrical contacts could be configured to include one or more springs or other elements that could be reversibly compressed. The first and second electrical contacts could be spring loaded in a direction perpendicular to an external surface of the body to which the housing 510a could be mounted. That is, the first and second electrical contacts could be spring loaded in order to improve and/or make more consistent an electrical connection between the first and second electrical contacts and skin of the first external body surface to which the housing 530a is mounted by the mount 520a. Alternatively, the first and/or second 530a electrical contacts could be fixed relative to housing 510a.

The housing 510a could be configured to be water-resistant and/or water-proof That is, the housing could be configured to include sealants, adhesives, gaskets, welds, press-fitted seams, and/or other joints such that the housing 510a is resistant to water entering an internal volume or volumes of the housing 510a when the housing 510a is exposed to water. The housing 510a could further be water-proof, i.e., resistant to water entering an internal volume or volumes of the housing 510a when the housing 510a is submerged in water. For example, the housing 510a could be water-proof to a depth of 1 meter, i.e., configured to resist water entering an internal volume or volumes of the housing 510a when the housing 510a is submerged to a depth of 1 meter. Further, the interface between the housing 510a and the first, second, and third 530a electrical contacts could be configured such that the combination of the housing 510a and the electrical contacts is water-resistant and/or water-proof.

The wearable device 500a includes electronics (not shown in FIG. 5) electronically coupled to the first, second, and third 530a electrical contacts. The electronics (e.g., electronics configured as a signal conditioner, impedance detector, capacitance detector, or otherwise as described herein) are configured to extract an electrocardiogram or other biosignal from voltage fluctuations between the two or more of the first, second, and third 530a electrical contacts (e.g., when the first, second, and third 530a electrical contacts are in contact with first and second external surfaces of the body). The electronics are further configured to detect an impedance between two or more of the first, second, and third 530a electrical contacts.

The wearable device 500a could be operated based an electrocardiogram, impedance, or other parameter detected as described herein. For example, the wearable device 500a could be configured to determine a health or other state of a wearer based on a detected electrocardiogram signal. Further, the wearable device 500a could be configured to determine whether the wearable device 500a is mounted to an external body surface of a wearer and/or that an electrocardiogram signal can be detected using the first, second, and third 530a electrical contacts based on an impedance and/or capacitance detected between two or more of the first, second, and third 530a electrical contacts.

The electronics or other elements of the wearable device 500a could be configured to prevent injury of a wearer and/or damage to the wearable device 500a due to operation of the device to extract an electrocardiogram or other biosignal from voltage fluctuations between two or more external body surfaces using the first, second, and third 530a electrical contacts. Clamping diodes and/or associated blocking resistors could be included in the wearable device 500a and configured to prevent voltages and/or currents above a certain specified maximum from being applied to the electrical contacts (and thus to the skin of the wearer) and/or to elements of the wearable device 500a (e.g., components (e.g., an ADC) of a signal conditioner, components of an impedance detector). A blocking capacitor (i.e., a capacitor having a high specified value of capacitance) could be electrically disposed between one or more or the electrical contacts and electronics of the wearable device 500a to prevent the wearable device 500a from injuring the skin of the external body surface(s) and/or causing electrochemical damage to the electrical contacts (e.g., by preventing the application of direct current to the skin for a protracted period of time, by ensuring that current injected into the skin through the electrical contacts is essentially balanced). Other operations and configurations of the wearable device 500a to prevent injury of a wearer and/or damage to the wearable device 500a are anticipated.

The first, second, and third 530a electrical contacts, and any additional electrical contacts (not shown) protruding from and or disposed on the housing 510a could additionally be used for other purposes. For example, electronics disposed in the wearable device 500a could be used to sense a skin resistance, a skin capacitance, a body water content, a body fat content, a Galvanic skin potential (GSP), an electromyographic (EMG) signal, and/or some other physiological signal present at and/or through the electrical contacts. Additionally or alternatively, the electrical contacts could be used to detect the presence of a charging device or some other electronic system electrically connected to the electrical contacts. The electronics could then use the electrical contacts to receive electrical energy from the charging device or other system to recharge a rechargeable battery of the wearable device 500a and/or to power the wearable device 500a. Such a rechargeable battery could additionally or alternatively be recharged wirelessly using electromagnetic energy received by a coil and other wireless charging circuitry disposed in the wearable device 500a.

Figure 5B:
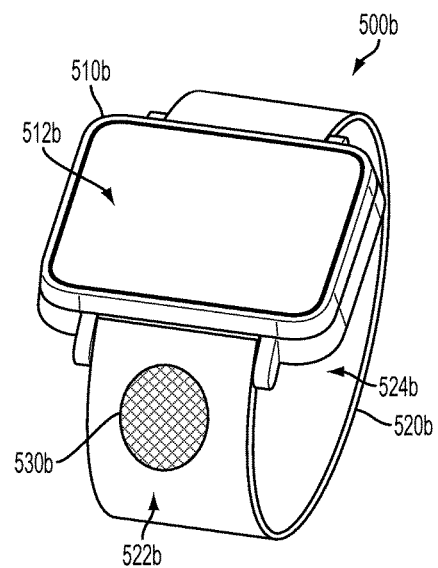
FIG. 5B is a perspective view of an example wearable device.

Alternatively, one or both of the electrical contacts of such a wearable device could be disposed on a band, strap, or other mount of the device. For example, FIG. 5B illustrates a wearable device 500b that can be configured to extract an electrocardiogram signal from voltage fluctuations between skin at first and second external body surfaces. A housing 510b is disposed on a mount 520b such that the housing 510b can be positioned on a first external surface of a first arm of the body (e.g., a surface of a wrist of the body). The housing 510b has an outside surface 512b that is away from the first external surface of the body and an inside surface (not shown) that is toward and/or in contact with the first external surface of the body when the housing 510b is positioned on the first external surface of the body. Similarly, the mount 520b has an inside surface 524b and an outside surface 522b. A third electrical contact 530b is disposed on the outside surface 522b of the mount 520b and configured to be contacted by skin of a second external body surface of a second arm of the body (i.e., an arm opposite an arm to which the wearable device 500b is mounted). Operated and/or mounted in this way, first and second electrical contacts (not shown) disposed on the inside surface of the housing 510b could contact skin at the first external surface of the body such that an electrocardiogram signal (as measured between the first and second external body surfaces, e.g., between a wrist of a first arm and a finger of a second, opposite, arm) could be extracted from voltage fluctuations between the third 530b electrical contact and at least one of the first and second electrical contacts.

Figure 5C:
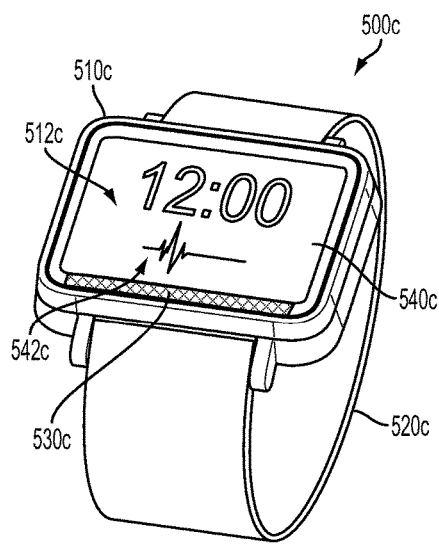
FIG. 5C is a perspective view of an example wearable device.

In some examples, such a wearable device could include a user interface configured to present and/or indicate information to a wearer and/or to receive information (e.g., command inputs) from the wearer. For example, FIG. 5C illustrates a wearable device 500c that can be configured to extract an electrocardiogram or other biosignal from voltage fluctuations between skin at first and second external body surfaces. A housing 510c is disposed on a mount 520c such that the housing 510c can be positioned on a first external surface of a first arm of the body (e.g., a surface of a wrist of the body). The housing 510c has an outside surface 512c that is away from the first external surface of the body and an inside surface (not shown) that is toward and/or in contact with the first external surface of the body when the housing 510c is positioned on the first external surface of the body. First and second electrical contacts (not shown) is disposed on the inside surface of the housing 510c and a third electrical contact 530c is disposed on the outside surface 512c of the housing 510c. Further, the wearable device 500c includes a user interface 540c disposed on the outer surface 512c of the housing.

A wearer of the device 500c may receive one or more recommendations or alerts generated from a remote server or other remote computing device, or from a processor within the device via the user interface 540c. The alerts could be any indication that can be noticed by the person wearing the wearable device. For example, the alert could include a visual component (e.g., textual or graphical information on a display), an auditory component (e.g., an alarm sound), and/or tactile component (e.g., a vibration). Further, the user interface 540c may be configured and/or operated to provide a visual display 542c to provide an indication of a status of the device, a time, a detected electrocardiogram or other biosignal, a detected impedance between two or more of the electrical contacts, or an indication of any other measured physiological parameters measured by the device 500c. Further, the user interface 540c may include one or more buttons and/or be configured as a touch screen for accepting inputs from the wearer. For example, user interface 540c may be configured to change the text or other visual information 542c in response to the wearer touching one or more locations of the user interface 540c.

Figure 5D:
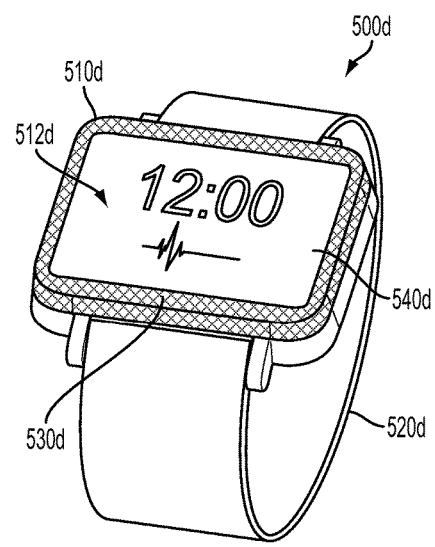
FIG. 5D is a perspective view of an example wearable device.

To allow for easier and/or more comfortable contact between an outward-facing electrode (e.g., 530a, 530b, 530c) and skin of an external body surface of a wearer (e.g., skin of a finger, hand, or other part of a wearer's body) and/or according to some other application, the size, shape, number, and/or disposition of such outward-facing electrode(s) could be different than shown above. For example, an outward-facing electrode could partially or completely encircle a band or strap of a wearable device, cover a larger area of an outside surface of a housing (e.g., completely cover such an outside surface), or be configured and/or disposed in some other way. For example, such an outward facing electrode could completely or partially encircle an outer edge of an outside surface of a housing of a wearable device and/or completely or partially encircle a display or other user interface element disposed on such an outside surface. For example, FIG. 5D illustrates a wearable device 500d that can be configured to extract an electrocardiogram signal from voltage fluctuations between skin at first and second external body surfaces. A housing 510d is disposed on a mount 520d such that the housing 510d can be positioned on a first external surface of a first arm of the body (e.g., a surface of a wrist of the body). The housing 510d has an outside surface 512d that is away from the first external surface of the body and an inside surface (not shown) that is toward and/or in contact with the first external surface of the body when the housing 510d is positioned on the first external surface of the body. First and second electrical contacts (not shown) are disposed on the inside surface of the housing 510d. A user interface 540d is disposed on the outside surface 512d of the housing 510d A third electrical contact 530d is disposed along an edge of the outside surface 512d of the housing 510d completely enclosing the user interface 540d.

Other configurations of a wearable device configured to detect and electrocardiogram or other biosignal from two or more skin locations of the body of a wearer and to detect an impedance between two or more electrical contacts are anticipated. Such wearable devices could include more than three electrodes configured to provide additional information to extract additional biosignals, to extract higher-quality (e.g., higher-magnitude, higher signal-to-noise-ratio) biosignals, to detect a Galvanic skin resistance, to detect a Galvanic skin response, to detect an EMG signal (e.g., an EMG signal from muscles in a wrist of a wearer), or to enable some other application. In some examples, an electrical contact could additionally be configured to detect contact with skin (e.g., a finger) of the wearer and the wearable device could operate responsive to such a detection, e.g., to extract an electrocardiogram signal from voltage fluctuations between the electrical contact and some other electrical contact(s). Additionally or alternatively, touch detection by an electrical contact could be used to receive an input from the wearer, e.g., to act as a 'button press' or other indication of a wearer's intent. Further, a wearable device could include multiple such electrical contacts configured to detect skin contact (e.g., to initiate detection of an electrocardiogram, to determine user input) and to enable detection of electrocardiograms or other biosignals. Additionally or alternatively, such an electrode could form a transparent or semi-transparent layer disposed on a display of the wearable device. For example, a layer of indium-tin-oxide, an array of fine wires or other conductive elements, or some other elements could be disposed on a display and configured to act as an electrical contact. Additionally or alternatively, an electrode of a touchscreen could be configured to capacitively couple with voltage fluctuations of a skin location of a wearer such that an electrocardiogram signal could be extracted from voltage fluctuations between the touchscreen electrode and some other electrical contact(s) of the wearable device.

In some examples, the wearable device (e.g., a housing 510a, 510b, 510c, 510d of the wearable device 500a, 500b, 500c, 500d) further includes at least one detector for detecting at least one other physiological parameter, which could include any parameters that may relate to the health of the person wearing the wearable device and/or the environment of the wearable device. For example, the detector could be configured to measure acceleration of the wearable device, a magnetic field, an electric field, an ambient light, a respiration rate, a skin temperature, etc. At least one of the detectors could be configured to non-invasively measure a volume of blood circulating in subsurface vasculature proximate to the wearable device. In a non-exhaustive list, the detector may include any one of an optical (e.g., CMOS, CCD, photodiode), acoustic (e.g., piezoelectric, piezoceramic), electrochemical (voltage, impedance), thermal, mechanical (e.g., pressure, strain, acceleration, rotation), magnetic, or electromagnetic (e.g., RF, magnetic resonance) sensor. In some examples, operation of such sensors to detect corresponding signals could occur responsive to a determination, based on a detected impedance between electrical contacts of the device (e.g., based on a determination that such a detected impedance is below a specified threshold and/or has remained below a threshold for a specified period of time), that the device is securely mounted to skin of a wearer.

In an example, a wearable device could be configured to extract an electrocardiogram signal from voltage fluctuations between two or more skin locations of a wearer. The wearable device could be further configured to detect a volume of blood in a portion of subsurface vasculature of the wearer at a plurality of points in time (e.g., by illuminating the portion of subsurface vasculature and detecting light responsively received from the portion of subsurface vasculature, i.e., via photoplethysmography) to generate a waveform of the volume of blood in the portion of subsurface vasculature over time (e.g., a photoplethysmographic signal). Time differences or other comparisons of features of the detected electrocardiogram signal and the determined volume waveform (e.g., a time difference between a maximum of the volume waveform and a corresponding QRS complex of the electrocardiogram signal) could be used to determine a flow rate, a pressure wave speed and/or latency, a pulse transit time, a blood pressure, an arterial stiffness, or other information about the blood in the portion of subsurface vasculature and/or information about the heart and vasculature of the wearer. Further, such determined information could be used to determine a health or medical state of the wearer, e.g., to determine a degree of atherosclerosis of the vasculature of the wearer.

Further, a wearable device as described herein could be modular. That is, one or more components of such a wearable device could be replaceable, extensible, and/or otherwise reconfigurable to add and/or remove capabilities of the wearable device. For example, a wearable device could include a housing containing a battery, a communications interface, a touchscreen user interface, and general-purpose electronics to enable a variety of applications of a wearable device. The wearable device could further include a modular mount configured to mount the housing to an external body surface and to enable some applications of the wearable device, e.g., by including one or more sensors. For example, a first modular mount could be configured to mount the housing around a wrist of a wearer and to enable extraction of an electrocardiogram signal from voltage fluctuations between the arms of a wearer by providing an electrical contact on an outside surface of the mount (e.g., an outer surface of a frame encircling the housing) to complement one or more electrical contacts provided by the housing on an inside surface of the housing. A second modular mount could be configured to mount the housing around the chest of a wearer and to enable detection of breathing patterns of the wearer by providing a strain sensor in a band of the mount that encircles the chest of the wearer.

Figure 6A:
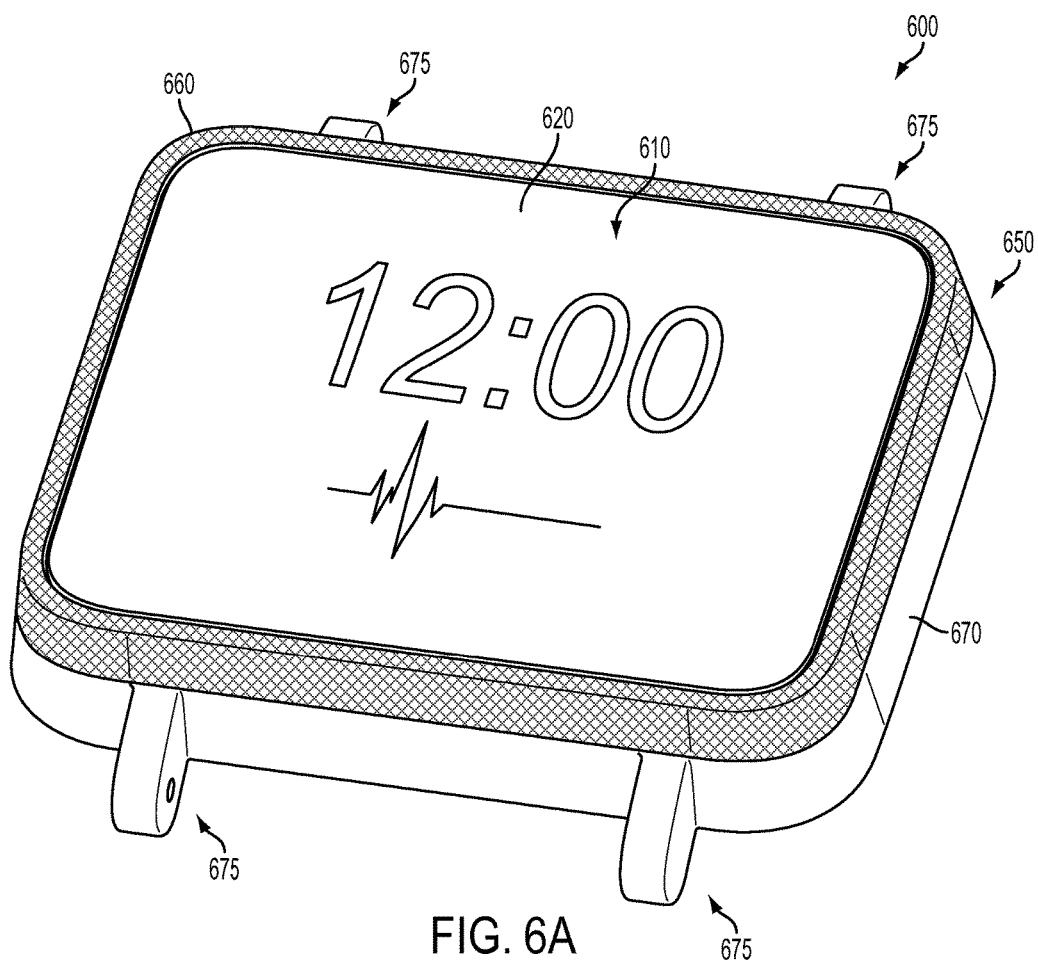
FIG. 6A is a top perspective view of elements of an example wearable device.

FIG. 6A illustrates a top perspective view of an example wearable device 600 including a central housing 610 configured to be removably seated in a frame 650 of a modular mount. The modular mount additionally includes a band (not shown) connected to the frame 650 and configured to mount the central housing 610 to an external body surface (e.g., a wrist) of a wearer. The central housing 610 includes a user interface 620 disposed on an outer surface of the central housing 610 (e.g., a surface opposite the external body surface when the central housing 610 is mounted to the external body surface by the modular mount). The user interface 620 is a touchscreen interface, configured to present visual indications to a wearer (e.g., by spatially modulating an emitted light of the user interface 620 and/or by spatially modulating a reflectivity of the user interface 620). The frame 650 includes a nonconductive inner portion 670 and a conductive outer portion 660. The outer portion 660 is configured to act as an electrical contact and to contact skin of an external body surface of the wearer (e.g., skin of a finger of the wearer). The outer portion 660 encircles the user interface 620 when the central housing 610 is seated in the frame 650 (as shown in FIG. 6A). The inner portion 670 of the frame 650 includes mounting points 675 configured to attach a band, strap, or other means of securing the wearable device 600 to an external body surface (e.g., the mounting points 675 could be configured to attach to a standard watch band, i.e., they could be approximately 26 millimeters apart, 20 millimeters apart, or some other distance apart according to a stand watch band size).

Figure 6B:
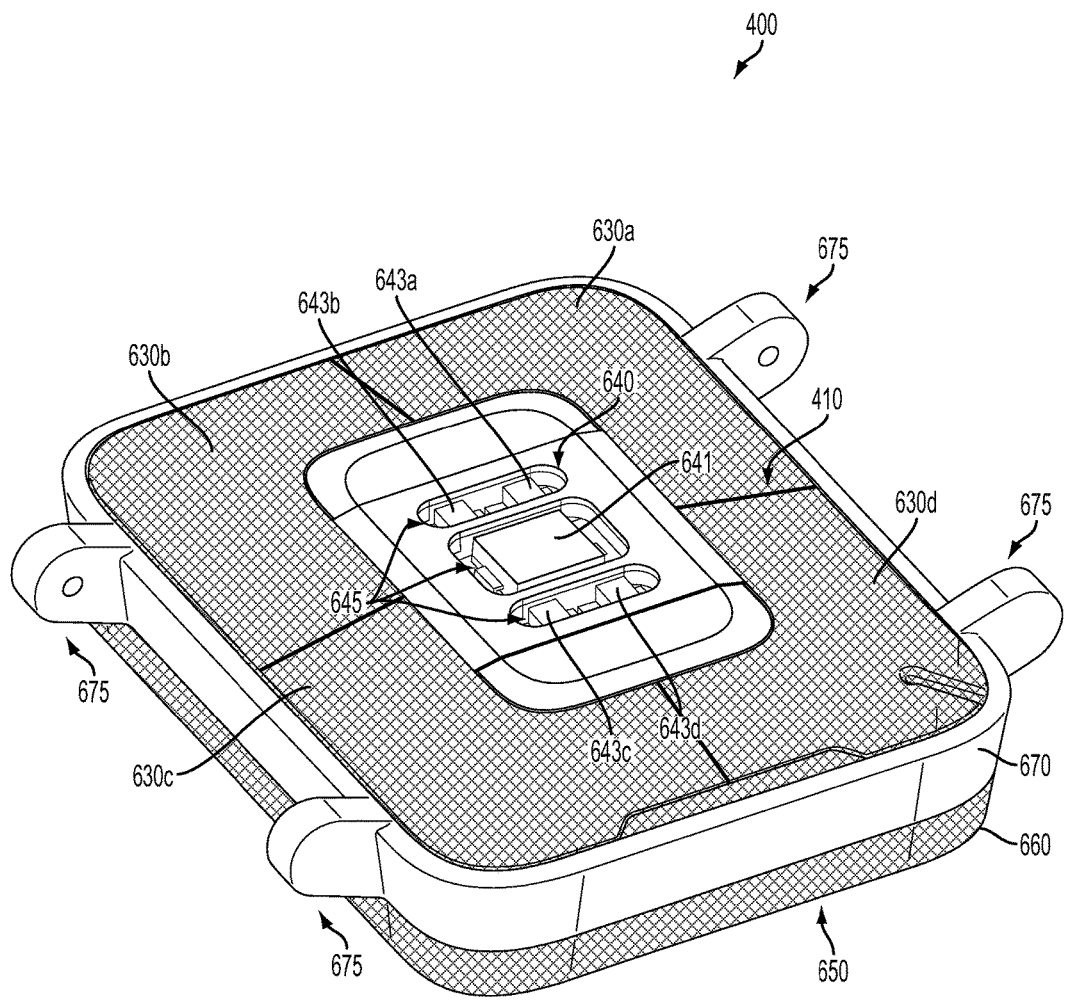
FIG. 6B is a bottom perspective view of the elements of the example wearable device illustrated in FIG. 6A.

FIG. 6B illustrates a bottom perspective view of the wearable device 600 illustrating elements disposed on an inside surface of the central housing 610 (i.e., elements disposed toward the external body surface when the central housing 610 is mounted to the external body surface by the modular mount). A plurality of electrical contacts 630a, 630b, 630c, 630d are disposed on the inside surface of the central housing 610. The plurality of electrical contacts 630a, 630b, 630c, 630d could be configured to enable a variety of applications of the wearable device 600. For example, pairs of the electrical contacts 630a, 630b, 630c, 630d could be operated to detect impedances (that is, impedances between the pairs of electrical contacts that are related, e.g., to how securely the device 600 is mounted to a skin surface), a skin resistance, a skin capacitance, a Galvanic skin response, a body water content, a body fat content, or other information by passing a current through and/or applying a voltage to skin proximate to the wearable device and detecting a corresponding voltage across and/or current through the pairs of the electrical contacts 630a, 630b, 630c, 630d. Further, a Galvanic skin voltage, an electrocardiogram signal, an electromyogram signal, or some other electrophysiological voltage signal could be detected through two or more of the electrical contacts 630a, 630b, 630c, 630d. In some examples, an electro-haptic stimulus could be delivered to a wearer though two or more of the electrical contacts 630a, 630b, 630c, 630d. In some examples, a temperature sensor could be thermally coupled to one or more of the electrical contacts 630a, 630b, 630c, 630d to enable the detection of the temperature of skin proximate to the one or more electrical contacts 630a, 630b, 630c, 630d.

An electrocardiogram or other biosignal could be extracted from voltage fluctuations between the outer portion 660 of the frame and one or more electrical contacts 630a, 630b, 630c, 630d when the central housing 610 is mounted to a first external body surface (e.g., skin of a wrist of a first arm of a wearer) and a second body surface (e.g., skin of a finger of an arm of the wearer opposite the arm to which the wearable device is mounted) is in contact with the outer portion 660 of the frame 650. Other operations of the wearable device 600 to extract an electrocardiogram or other biosignals of a wearer, as described herein or otherwise, are anticipated.

The central housing 610 additionally includes an optical sensor 640. The optical sensor 640 includes a photodetector 641 and four light sources 643a, 643b, 643c, 643d. The photodetector 641 and light sources 643a, 643b, 643c, 643d are disposed behind protective windows 645. The four light sources 643a, 643b, 643c, 643d could be similarly or differently configured. The photodetector could be any element configured to electronically detect one or more properties (e.g., wavelength, spectral profile, amplitude, amplitude within a specified range of wavelengths) of received light (e.g., a photodiode, a phototransistor, a photoresistor, an avalanche photodiode). The four light sources 643a, 643b, 643c, 643d could include LEDs, lasers, or other elements configured to emit light. Further, the four light sources 643a, 643b, 643c, 643d could be configured to emit light having one or more specified properties (e.g., a specified wavelength, a specified amplitude, a specified waveform over time, a specified pulse or other timing). The optical sensor 640 could be configured to illuminate target tissues (e.g., using the light sources 643a, 643b, 643c, 643d) and to detect light responsively or otherwise emitted from the target tissue (e.g., using the photodetector 641) to detect one or more properties of the target tissue.

Figure 6C:
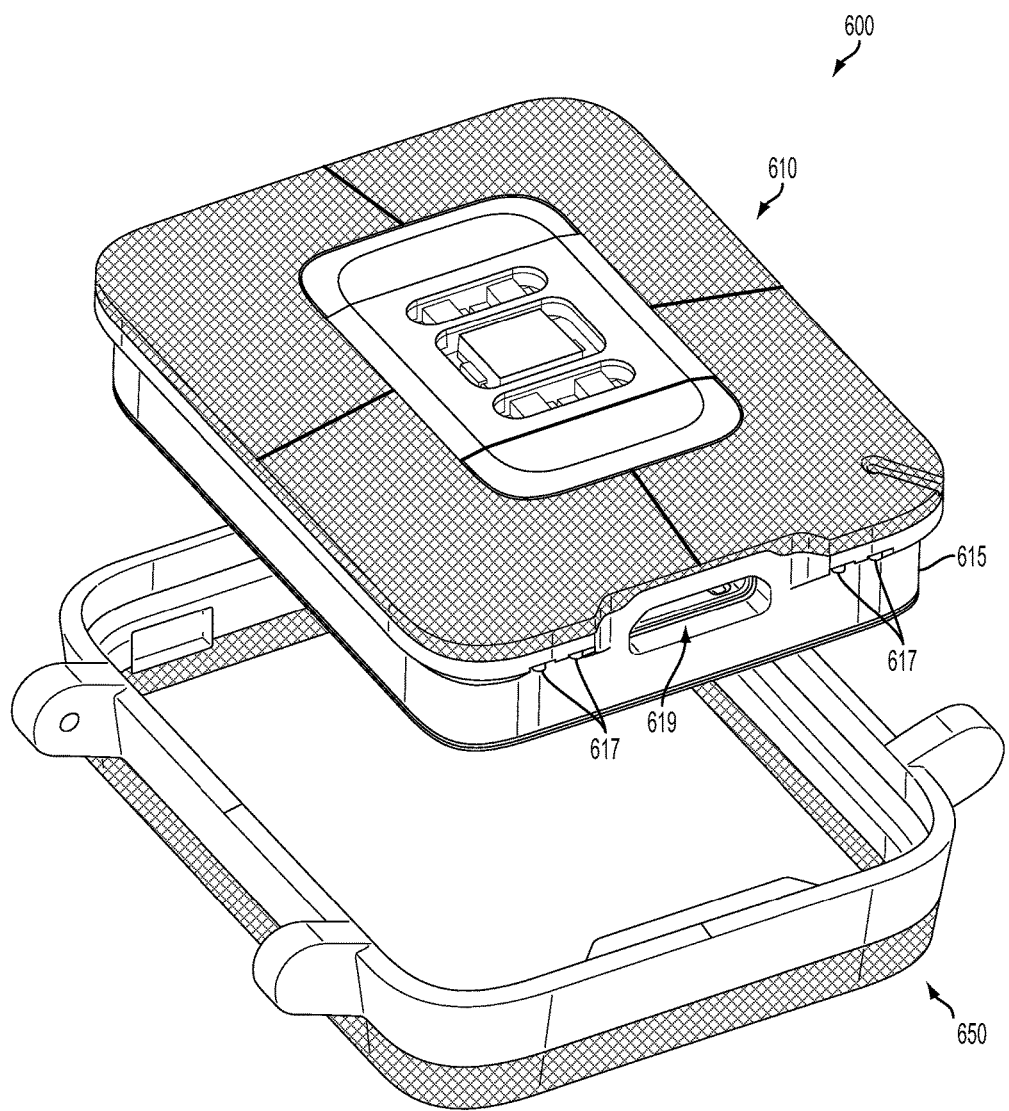
FIG. 6C is a bottom perspective view of the elements of the example wearable device illustrated in FIG. 6A, when a housing and a frame of the elements are disengaged from each other.

FIG. 6C illustrates a bottom perspective view of the wearable device 600 when the central housing 610 has been unseated from the frame 650. FIG. 6C illustrates a nonconductive housing 615, a wired interface 619, and contact pads 617 of the central housing. The wired interface 619 could be any interface configured to receive one or more conductors configured, e.g., as a connector such that power and electronic signals may be transmitted to and/or received from electronics disposed in the central housing 610. For example, the wired interface 619 could be a micro-USB interface. The contact pads 617 are configured to allow electrical contacts between electronics of the central housing 610 and electronics or other elements of a modular frame (e.g., the conductive electrical contact formed by the outer portion 660 of the frame 650).

Note that the contact pads 617 could be electrically connected within the central housing 610 or could be electrically independent. That is, the contact pads 617 could be electrically connected together such that the contact pads 617 cannot be used to transfer different electrical signals. Alternatively, the contact pads 617 could be electrically distinct (e.g., could be connected to separate components of electronics within the central housing 610) and thus could be used to transfer different electrical signals. For example, the four contact pads 617 could be connected to respective four distinct electrical contacts or electrodes of a modular frame into which the central housing 610 could be removably seated. Additionally or alternatively, a modular frame could electrically connect one or more of the four contact pads 617 together according to some application. For example, a first contact pad could be configured to detect a voltage, a second contact pad could be configured to source and/or sink a specified current, and the modular frame could connect the first and second contact pads to a single electrical contact to enable the determination of a resistance of some target (e.g., of a portion of skin, by determining a voltage across the portion of skin related to the specified current injected into the portion of skin).

In some applications, two of the contact pads 617 could be configured to provide power to a component of the modular mount, and the remaining two contact pads 617 could be configured to transmit and/or receive data to/from elements of the modular mount (e.g., an active sensor of the modular mount). Additionally or alternatively, such a configuration of the contact pads 617 could be used to facilitate communication between the central housing 610 and some other system, e.g., to facilitate reprogramming of electronics of the central housing 610, to facilitate data transfer of logged data stored in a data storage of the central housing, or some other application. Additional or alternative configurations and applications of the contact pads 617 and of the central housing 610 are anticipated.

FIG. 7 is a simplified schematic of a system 700 including one or more wearable devices 710. The one or more wearable devices 710 may be configured to transmit data via a communication interface 715 over one or more communication networks 720 to a remote server 730. In one embodiment, the communication interface 715 includes a wireless transceiver for sending and receiving communications (e.g., indications of measured electrocardiograms, impedances, or other signals) to and from the server 730. In further embodiments, the communication interface 715 may include any means for the transfer of data, including both wired and wireless communications. For example, the communication interface 715 may include a universal serial bus (USB) interface or a secure digital (SD) card interface. Communication networks 720 may include any of: a plain old telephone service (POTS) network, a cellular network, a fiber network and a data network. The server 730 may include any type of remote computing device or remote cloud computing network. Further, communication network 720 may include one or more intermediaries, including, for example wherein the wearable device 710 transmits data to a mobile phone or other personal computing device, which in turn transmits the data to the server 730.

In addition to receiving communications from the wearable device 710, such as data regarding health and/or affect state as input by the user or detected electrocardiographic (ECG) signals, the server may also be configured to gather and/or receive either from the wearable device 710 or from some other source, information regarding a wearer's overall medical history, environmental factors and geographical data. For example, a user account may be established on the server for every wearer that contains the wearer's medical history. Moreover, in some examples, the server 730 may be configured to regularly receive information from sources of environmental data, such as viral illness or food poisoning outbreak data from the Centers for Disease Control (CDC) and weather, pollution and allergen data from the National Weather Service. Further, the server may be configured to receive data regarding a wearer's health state from a hospital or physician. Such information may be used in the server's decision-making process, such as recognizing correlations and in generating clinical protocols.

Additionally, the server may be configured to gather and/or receive the date, time of day and geographical location of each wearer of the device during each measurement period. If measuring physiological parameters of the user (e.g., electrocardiograms), such information may be used to detect and monitor spatial and temporal spreading of diseases. As such, the wearable device may be configured to determine and/or provide an indication of its own location. For example, a wearable device may include a GPS system so that it can include GPS location information (e.g., GPS coordinates) in a communication to the server. As another example, a wearable device may use a technique that involves triangulation (e.g., between base stations in a cellular network) to determine its location. Other location-determination techniques are also possible.

Further, some embodiments of the system may include privacy controls which may be automatically implemented or controlled by the wearer of the device. For example, where a wearer's collected data are uploaded to a cloud computing network for analysis by a clinician, the data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined.

Additionally or alternatively, wearers of a device may be provided with an opportunity to control whether or how the device collects information about the wearer (e.g., information about a user's medical history, social actions or activities, profession, a user's preferences, or a user's current location), or to control how such information may be used. Thus, the wearer may have control over how information is collected about him or her and used by a clinician or physician or other user of the data. For example, a wearer may elect that data, such as health state and physiological parameters, collected from his or her device may only be used for generating an individual baseline and recommendations in response to collection and comparison of his or her own data and may not be used in generating a population baseline or for use in population correlation studies.

IV. Example Components Disposed in a Wearable Device

FIG. 8 is a simplified block diagram illustrating the components of a wearable device 800, according to an example embodiment. Device 800 may take the form of or be similar to the wearable devices 100, 400a, 400b, 400c, 400d, 600 shown in FIGS. 1A-B, 400A, 400B, 400C, 400D, and 600A-C, respectively. However, wearable device 800 may also take other forms, such as an ankle, waist, or chest-mounted device. Alternatively, devices as described herein could take the form of a device that is not configured to worn on a body. For example, device 800 could take the form of a handheld device configured to be maintained in proximity to an environment of interest (e.g., a body part, a biological sample container, a volume of a water treatment system) by a user or operator of the device 800 or by a frame or other supporting structure. Device 800 also could take other forms. In particular, FIG. 8 shows an example of a device 800 having three electrical contacts 810a, 810b, 810c connected to biopotential sensor 820. The electrical contacts 810a, 810b, 810c are configured to electrically connect to external body surfaces (e.g., the surface of skin) when placed in contact with (e.g., mounted to) such surfaces. In an example, first 810a and second 810b electrical contacts could be disposed on a housing of the device 800 such that they contact skin locations on a wrist of a wearer when the housing is mounted to the wrist. The third electrical contact 810c can be contacted by skin (e.g., of a fingertip) of an arm of the wearer that is opposite to arm to which the housing is mounted. The device 800 further includes a user interface 830, communication interface 840 for transmitting and/or receiving data to/from a remote system, and a controller 850. The components of the device 800 may be disposed on a mount or on some other structure for mounting the device to a location of interest, e.g., to a location (e.g., a wrist) of a body of a wearer of the device 800.

Controller 850 may be provided as a computing device that includes one or more processors 860. The one or more processors 860 can be configured to execute computer-readable program instructions 880 that are stored in the computer readable data storage 870 and that are executable to provide the functionality of a device 800 described herein.

The computer readable medium 870 may include or take the form of one or more non-transitory, computer-readable storage media that can be read or accessed by at least one processor 860. The one or more computer-readable storage media can include volatile and/or non-volatile storage components, such as optical, magnetic, organic or other memory or disc storage, which can be integrated in whole or in part with at least one of the one or more processors 860. In some embodiments, the computer readable medium 870 can be implemented using a single physical device (e.g., one optical, magnetic, organic or other memory or disc storage unit), while in other embodiments, the computer readable medium 870 can be implemented using two or more physical devices.

The biopotential sensor 820 could include a variety of components configured in a variety of ways to allow detection of impedances between two or more of the electrical contacts 810a, 810b, 810c, to allow detection of electrocardiogram signals from voltage fluctuations between two or more of the electrical contacts 810a, 810b, 810c when the electrical contacts 810a, 810b, 810c are contacting appropriate respective skin locations of a wearer and/or to allow other operations and applications. The biopotential sensor 820 could include analog and/or digital electronic components to enable analog and/or digital manipulations of electrical signals related to voltage fluctuations between the electrical contacts 810a, 810b, 810c. The biopotential sensor 820 could further include analog and/or digital electronic components to enable application of currents and/or voltages through/across the electrical contacts 810a, 810b, 810c to allow for detection of impedances or other properties between the electrical contacts 810a, 810b, 810c.

Generally, the biopotential sensor 820 includes components configured to amplify and filter voltage fluctuations between the electrical contacts 810a, 810b, 810c. The biopotential sensor 820 could include one or more amplifiers, buffers, filters, operational amplifiers, resistors, capacitors, inductors, transistors, rectifiers, or some other linear or nonlinear electronic component or combinations thereof. Such components could be formed as a number of discrete signal processing blocks (e.g., discrete sets of components configured to perform some operation(s) on electronic input(s) to form electronic output(s)) that are connected together (e.g., the output(s) of a first block form the input(s) of one or more other blocks).

In some embodiments, the biopotential sensor 820 could be configured to generate an electronic signal (e.g., to generate a detected electrocardiogram) that is related to a band-passed version of the voltage fluctuations between two or more of the electrical contacts 810a, 810b, 810c. This could include applying the voltage fluctuations to a band-pass filter having a pass-band between approximately 0.05 Hertz and approximately 150 Hertz. The biopotential sensor 820 could additionally apply a notch filter (at, e.g., approximately 60 Hertz) to remove some narrow-band signal from the voltage fluctuations (e.g., to remove approximately 60 Hertz noise emitted by power mains in the environment of the wearable device 800). Additionally or alternatively, an electronic signal could be digitally sampled and some digital filtering could be performed (e.g., by the processor(s) 860) to generate an electrocardiogram or other biopotential signal. In such examples, the controller 850 and elements thereof (e.g., an ADC of the processor(s) 860) could be considered part of an overall biopotential sensor configured to detect an electrocardiogram or other biosignal waveform from voltage fluctuations between the electrical contacts 810a, 810b, 810c.

The biopotential sensor 820 could include a fast response circuit or other circuitry or components configured to allow the biopotential sensor 820 to extract an electrocardiogram or other biosignal after the voltage fluctuations between the electrical contacts 810a, 810b, 810c exhibit a large change (e.g., a change in baseline voltage level, a spike or other transient related to an electrostatic discharge, a skin location coming into contact with one of the electrical contacts, and/or a skin location moving relative to one or both of the electrical contacts 810a, 810b, 810c). For example, the biopotential sensor 820 could be configured to determine that one or more elements (e.g., amplifiers, op-amps, signal processing blocks) of the biopotential sensor 820 are electronically saturated (i.e., outputting a maximal and/or minimal signal level, or having an internal signal that has a maximal or minimal value) and to responsively control one or more properties of the biopotential sensor 820 to reduce the electronic saturation of the one or more elements of the biopotential sensor 820.

The biopotential sensor 820 could include circuitry or other elements configured to detect and/or determine whether the electrical contacts 810a, 810b, 810c are in contact with skin and/or that an electrocardiogram or other biosignal can be extracted from voltage fluctuations between them 810a, 810b, 810c and/or using some other sensor(s) of the device 800. This could include detecting an impedance between two or more of the electrical contacts (e.g., between the first 810a and second 810b electrical contacts). The biopotential sensor 820 could include circuitry (e.g., voltage dividers, relaxation oscillators, current injectors) configured to actively or passively detect an effective impedance (e.g., a resistance and/or capacitance) between the first and second electrical contacts 810*a*, 810*b* that could be used to determine that the first and second electrical contacts 810*a*, 810*b* are in contact with skin and/or that an electrocardiogram or other biosignal can be detected therefrom. Such circuitry could additionally be configured and/or operated to detect other properties of a wearer, e.g., a body water content, a body fat content. Additionally or alternatively, the biopotential sensor 820 could include circuitry (e.g., comparators, Schmitt triggers, overvoltage sensors, differentiators, fast response circuitry) configured to detect electrostatic discharges, voltage transients, changes in voltage offsets, or other properties of voltage fluctuations between the electrical contacts 810*a*, 810*b*, 810*c* that are related to the electrical contacts 810*a*, 810*b*, 810*c* coming into and/or leaving contact with skin of a wearer.

In some examples, the biopotential sensor 820 could include circuitry to protect elements of the wearable device 800 (e.g., to protect amplifiers, filters, voltage sensors, or other elements of the biopotential sensor 820) from high voltages and/or currents present across and/or through the electrical contacts 810*a*, 810*b*, 810*c*. For example, the biopotential sensor 820 could include clamping diodes, blocking resistors, blocking capacitors, electronic switches, or other elements configured to prevent components of the biopotential sensor 820 from being damaged by voltages and/or currents at/through the electrical contacts 810*a*, 810*b*, 810*c*. These elements of the biopotential sensor 820 could be configured to protect the wearable device 800 from electrostatic discharges from the environment of the wearable device 800.

The program instructions 880 stored on the computer readable medium 870 may include instructions to perform any of the methods described herein. For instance, in the illustrated embodiment, program instructions 880 include a controller module 882, a calculation and decision module 884, and an alert module 886.

Controller module 882 may include instructions for operating the biopotential sensor 820 and/or other components (e.g., an optical or other sensor of the wearable device 800) to generate data related to one or more properties (e.g., physiological and/or hemodynamic parameters) of a body and/or of the device 800. This could include operating the biopotential sensor to detect an impedance between two or more of the electrical contacts, to detect a voltage between two of the electrical contacts, or to perform some other measurement or function using the electrical contacts. In some examples, such operation could include detecting an impedance between the first 810*a* and second 810*b* electrical contacts. In some examples, such operation could include detecting an electrocardiogram by detecting a voltage between the third 810*c* electrical contact and at least one of the first 810*a* and second 810*b* electrical contacts when the first 810*a* and second 810*b* electrical contacts are mounted in contact with skin of a wrist of a wearer and the third electrical contact 810*c* is being contacted by a finger or other skin of an arm of the wearer opposite the wrist.

The calculation and decision module 884 may include instructions for using information (e.g., electrocardiograms or other biosignals, impedances) detected using the biopotential sensor 820 to determine one or more hemodynamic or other physiological parameters of a user. Such determinations could include detecting peaks, maxima, minima, or other features of an electrical signal detected using biopotential sensor 820. Such determinations could further include determining a pulse rate, pulse timing, pulse variability, or other hemodynamic properties of a user by, e.g., determining properties of one or more peaks or other features of detected electrical or other signals. Such determinations could also include determinations based on a detected impedance between two or more of the electrical contacts (e.g., between the first 810*a* and second 820*b* electrical contacts).

In some examples, the calculation and decision module 884 may include instructions for determining whether the device 800 is mounted to a skin surface, to determine whether the device is securely mounted to such a surface, to determine whether the device has been securely mounted to such a skin surface for a specified period of time, to determine whether an electrical connection between the first 810*a* and second 810*b* electrical contacts is sufficient to detect an electrocardiogram or other biosignal using at least one of the first 810*a* and second 810*b* electrical contacts, or according to some other application. Responsive to such determinations, an indication could be provided to a user to re-position or re-mount the device 800 (e.g., to improve the an electrical connection between the electrical contacts and skin of the wearer), an indication could be provided to a user to contact one or more of the electrical contacts (e.g., 810*c*) with a finger or other skin surface to allow for detection of an electrocardiogram or other biopotential (e.g., between the third electrical contact 810*c* and at least one of the first 810*a* and second 810*b* electrical contacts), an electrocardiogram or other biosignal could be detected using the biopotential sensor 820 or some other components of the device 800, or some other operations could be performed.

The controller module 882 can further include instructions for operating a user interface 820. For example, controller module 882 may include instructions for displaying data collected using the biopotential sensor 820 analyzed by the calculation and decision module 884, or for displaying one or more alerts generated by the alert module 886. The controller module 882 can include instructions for operating the user interface 830 based on a determination of the calculation and decision module 884 (e.g., a determined pulse rate, blood pressure, pulse transit time, arterial stiffness, blood oxygenation, or other hemodynamic and/or physiological parameters). Controller module 882 may include instructions for displaying data related to a user account of a user, e.g., a number of unread emails in a user's email account, the content of an email received by the user, or some other information. Further, controller module 882 may include instructions to execute certain functions based on inputs accepted by the user interface 820, such as inputs accepted by one or more buttons disposed on the user interface.

Communication interface(s) 840 may also be operated by instructions within the controller module 882, such as instructions for sending and/or receiving information via a wireless antenna, which may be disposed on or in the device 800. The communication interface 840 can optionally include one or more oscillators, mixers, frequency injectors, etc. to modulate and/or demodulate information on a carrier frequency to be transmitted and/or received by the antenna. In some examples, the device 800 is configured to indicate an output from the processor by modulating an impedance of the antenna in a manner that is perceivable by a remote server or other remote computing device.

The computer readable medium 870 may further contain other data or information, such as medical and health history of a user of the device 800, user account information, user credentials (e.g., usernames, passwords, cryptographic keys and/or certificates), that may be useful in performing functions of the device 800. In some examples, the device 800 could be configured to detect one or more physiological and/or hemodynamic parameters of a user (e.g., a heart rate, a blood oxygenation, a blood pressure, the presence and/or concentration of one or more analytes in the blood of a wearer) and the computer readable medium 870 could contain information related to such physiological parameter detection (e.g., sensor calibration information, physiological parameter baselines of a user, physiological parameter levels indicative of a medical condition). The calculation and decision module 884 may be configured to use such stored information to determine whether a wearer is experiencing a medical condition and may further, upon determining that such a medical or other emergency condition is indicated, generate one or more recommendations for the user of the device 800 based, at least in part, on consultation of a clinical protocol. Such recommendations may alternatively be generated by a remote server and transmitted to the device 800.

In some examples, information collected by the device 800 (e.g., collected physiological parameter data, baseline profiles, health state information input by device users) may be input to a cloud network and be made available for download by a user's physician. Trend and other analyses may also be performed on the collected data, such as hemodynamic property data and health state information, in the cloud computing network and be made available for download by physicians or clinicians.

In response to a determination by the calculation and decision module 884 that a medical or other specified condition is indicated, the alert module 886 may generate an alert via the user interface 820. The alert may include a visual component, such as textual or graphical information displayed on a display, an auditory component (e.g., an alarm sound), and/or tactile component (e.g., a vibration). Such alerts could be generated responsive to determining that a detected impedance is below a specified threshold, above a specified threshold, has stabilized, or according to some other determination. The textual information may include one or more recommendations, such as a recommendation that the user of the device contact a medical professional, seek immediate medical attention, or administer a medication. The alert indication could include or indicate a recommendation that a user remove and reposition the device, tighten a strap of the device, or otherwise improve the mounting of the device to skin of the wearer, e.g., responsive to a determination that a detected impedance is greater than a specified threshold. The alert indication could include or indicate a recommendation that a user touch a finger to the device to allow for detection of an electrocardiogram between the finger and an opposite wrist to which the device is mounted, e.g., responsive to a determination that a detected impedance is less than a specified threshold. Additionally or alternatively, the alert module 886 may generate an alert via the communication interface(s) 840 such that the alert is communicated to a remote system, e.g., a server in a physician's office, emergency room, or other locations in a hospital, a server in an emergency medical services and/or police department dispatch office, or some other remote systems

V. Illustrative Methods for Operating a Wearable Device

Figure 9:
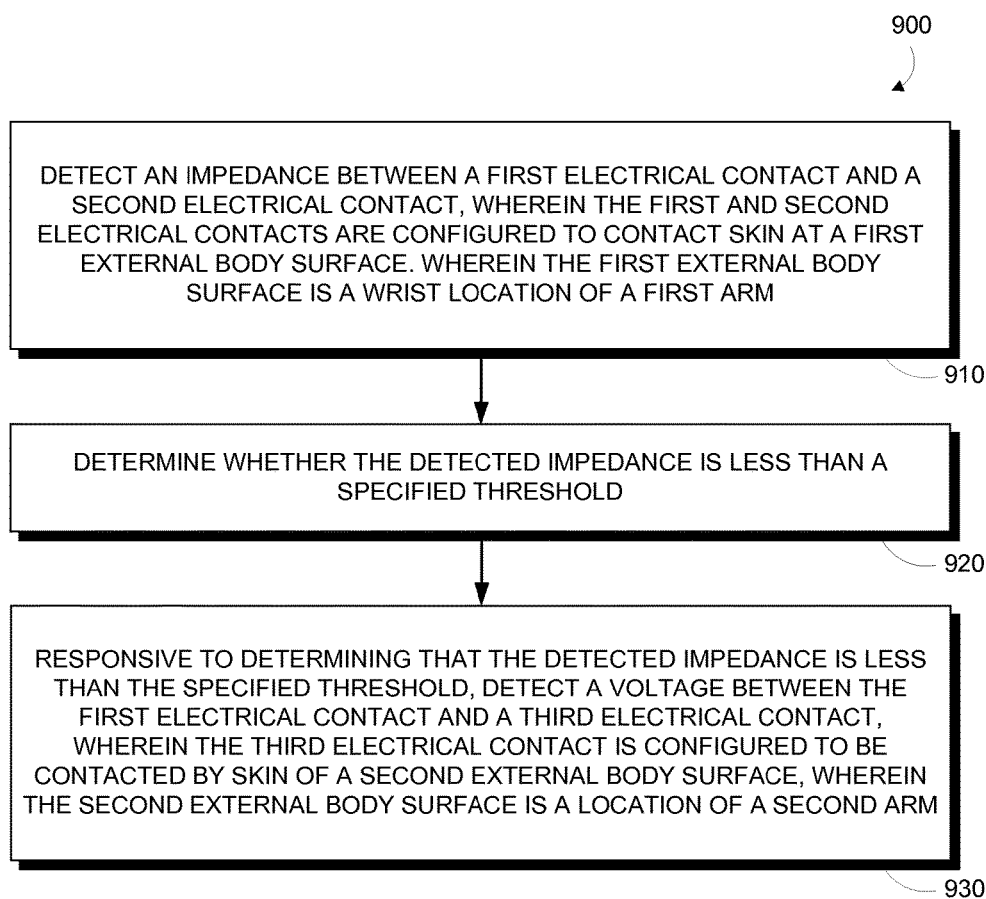
FIG. 9 is a flowchart of an example method.

FIG. 9 is a flowchart of a method 900 for operating a wearable device. The operated wearable device includes (i) a housing, (ii) a mount configured to mount the housing to a first external body surface (e.g., a wrist location of a first arm of a wearer), (iii) first and second electrical contacts disposed on the housing and configured to contact skin at the first external body surface when the housing is mounted on the first external body surface, and (iv) a third electrical contact that is disposed on the housing and that is configured to be contacted by skin of a second body surface located on a second arm of the wearer.

The method 900 includes detecting an impedance between the first electrical contact and the second electrical contact (910). This could include applying a specified voltage and/or current between/through the electrical contacts and an amplitude, time dependence, or other properties of a current/voltage responsively developed through/between the electrical contacts could be detected and used to determine the impedance. The applied specified voltage and/or current could have a specified waveform or other property of variation over time, e.g., a specified frequency, pulse width, pulse repetition frequency, pulse rise time, or other properties. In a particular example, a capacitor could be electrically connected between the first and second electrical contacts. The capacitor could be charged (e.g., charged to a specified voltage) during a first period of time and subsequently discharged through the first and second electrical contacts (e.g., through skin to which the electrical contacts are mounted). A voltage across and/or a current through the capacitor could be measured during the discharge to determine an impedance (e.g., a DC impedance, a phase and magnitude of an AC impedance at one or more frequencies, an impedance spectrum, a resistive, capacitive, inductive, and/or reactive component of the impedance) between the first and second electrical contacts. The impedance between the first and second electrical contacts, or between some other pair of electrical contacts of a wearable device, could be detected in some other way.

The method 900 also includes determining whether the detected impedance is less than a specified threshold (920). This could comparing an ohmic, reactive, resistive, capacitive, inductive, or otherwise characterized electrical property describing the flow of current and/or the transfer of voltages between the first and second electrical contacts, that is, comparing come parameter of the detected impedance between the first and second electrical contacts. The specified threshold could be related to one or more properties of the wearable device, e.g., the threshold could be specified as a multiple or fraction of an input impedance of an amplifier, buffer, or other components that are electrically connected to the electrical contacts and that are configured to detect voltages or other electrical signals between the electrical contacts. In some examples, the threshold could be specified based on a previously detected impedance or some other consideration. For example, a first impedance could be detected at a first point in time and used to determine a threshold (e.g., by determining a fraction of the first impedance). A specified threshold could be determined based on a plurality of detected impedances and/or on a change in a detected impedance over time. For example, the wearable device could detect a level and a rate of change of an impedance during a first period of time and could determine a specified threshold based on such information, e.g., based on an expected long-term stable value of the impedance.

The method 900 also includes, responsive to determining that the detected impedance is less that the specified threshold, detecting a voltage between the first electrical contact and the third electrical contact (930). This could include sampling (e.g., using an ADC or other discrete-time device) a voltage between the first and third electrical contacts a plurality of times during a plurality of respective points in time. This could include amplifying, filtering, level-shifting, inverting, and/or performing some other operation on the voltage between the first and third electrical contacts using, e.g., one or more amplifiers, filters, op-amps, resistors, inductors, capacitors, other electronic element(s), and/or combinations thereof. A wearer could place skin of the second external body surface (e.g., a fingertip) of the wearer in contact with the third electrical contact before the voltage between the first electrical contact and the third electrical contact is detected (930). Placing skin of the second external body surface in contact with the third electrical contact could occur at the initiative of the wearer, e.g., in response to the wearer having performed and/or being about to perform a strenuous task (e.g., exercise), experiencing some symptoms (e.g., fatigue, nausea, vertigo, heart palpitations, orthostatic hypertension), having received and/or being about to receive a drug (e.g., having taken nitroglycerin). Additionally or alternatively, placing skin of the second external body surface in contact with the third electrical contact could occur in response to an indication (e.g., a vibration, a sound, a visual indication on a display of the wearable device, an indication through some other device in communication with the wearable device) that the wearer should perform such an action to enable the detection of an electrocardiogram or other biosignal by the wearable device. Such an indication could be provided in response to determining that the detected impedance is les that the specified threshold (e.g., the method 900 could further include, responsive to determining that the detected impedance is less that the specified threshold, providing an indication that the detected impedance is less than the specified threshold).

The method 900 could include additional steps. For example, the method 900 could include mounting the wearable device to the wrist location of the first arm of the wearer such that skin of the first external body surface is in contact with the first and second electrical contact. This could include encircling the wrist of the wearer with a band, strap, or other encircling element of the mount. This could include operating a clasp, snap, or other securing elements of the mount such that the wearable device is mounted to the wrist location (e.g., securing two halves of a flexible strap of the mount together around the wrist of the wearer). In some examples, the mount includes an adhesive, and mounting the wearable device to the first external body surface includes activating, applying, and/or exposing the adhesive and adhering the wearable device to the body surface. The method 900 could include providing an indication to a wearer that the wearable device is not correctly mounted to the wrist (or other skin surface location). For example, the method 900 could include, responsive to determining that the detected impedance is greater that a specified threshold, providing an indication that the detected impedance is greater than the specified threshold. The wearer could then act to remove and reposition the wearable device, reapply an adhesive, tighten a strap or other means for mounting the wearable device to skin, or otherwise re-mount the wearable device.

The method 900 could include additional steps relating to one or more detected voltages. In some examples, the method 800 could include indicating an electrocardiogram or other biosignal in the detected voltage(s) using a display disposed in the wearable device. In some examples, the method 900 could include wirelessly transmitting an electrocardiogram or other biosignal in the detected voltage(s) using a wireless transmitter disposed in the wearable device. For example, the wearable device could transmit a detected electrocardiogram waveform to a remote system (e.g., a server or cloud service accessible to a healthcare provider). In some examples, the method 900 could include logging or otherwise storing the detected voltage(s) and/or detected impedance(s) using a data storage disposed in the wearable device. In some examples, the method 900 could include operating the wearable device based on the detected voltage(s) and/or detected impedance(s). For example, the wearable device could be operated to generate an alert, send a transmission to a remote system, or some other action in response a detected electrocardiogram waveform and/or information related to a detected electrocardiogram waveform (e.g., if a Q-T interval of the a detected electrocardiogram waveform exceeds a threshold).

In some examples, the wearable device could include means for optically detecting the volume of blood in a portion of subsurface vasculature of the wearer at a plurality of points in time, and generating a blood volume waveform over time (i.e., a photoplethysmographic waveform) based on the plurality of detected volumes of blood. An individual such blood volume detection could include operating a light source of the wearable device to emit light into the portion of subsurface vasculature through overlying skin and operating a light sensor of the wearable device to receive light responsively reflected, scattered, or otherwise emitted from the portion of subsurface vasculature through the overlying skin. The method 900 could further include using the generated blood volume waveform, in combination with detected voltage(s) related to an electrocardiogram waveform, to determine a blood pressure of the wearer, a degree of atherosclerosis of the vasculature of the wearer, or some other health or medical state of the wearer. This could include determining time differences or other comparisons of features of the extracted ECG waveform and the generated blood volume waveform (e.g., a time difference between a maximum of the volume waveform and a corresponding QRS complex of the ECG waveform) to determine a flow rate, a pressure wave speed and/or latency, or other information about the blood in the portion of subsurface vasculature and/or information about the heart and vasculature of the wearer. Further, such an optical sensor, or some other sensor of the wearable device, could be operated to detect physiological parameters of the wearer responsive to a determination based on a detected impedance between the first and second electrical contacts (or between some other electrical contacts of the wearable device). For example, the wearable device could determine, based on a detected impedance, that the wearable device is securely mounted to a wearer and could responsively operate a sensor to detect a physiological parameter of the wearer.

The example method 900 illustrated in FIG. 9 is meant as an illustrative, non-limiting example. Additional or alternative elements of the method and additional or alternative components of the wearable device are anticipated, as will be obvious to one skilled in the art.

IV. Conclusion

Where example embodiments involve information related to a person or a device of a person, the embodiments should be understood to include privacy controls. Such privacy controls include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

The particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

Additionally, while various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. Other embodiments may be used, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

What is claimed is:

1. A wearable device comprising:
   a housing;
   a user interface disposed on an outside surface of the housing;
   a mount configured to mount the housing to a first external body surface;
   a first electrical contact disposed on the housing, wherein the first electrical contact is configured to contact skin at the first external body surface when the housing is mounted on the first external body surface, wherein the first external body surface is a wrist location of a first arm of a wearer;
   a second electrical contact disposed on the housing, wherein the second electrical contact is configured to contact skin at the first external body surface when the housing is mounted on the first external body surface;
   a third electrical contact disposed on the housing, wherein the third electrical contact is configured to be contacted by skin of a second external body surface, wherein the second external body surface is a location of a second arm of the wearer; and
   a controller, wherein the controller is configured to perform controller operations comprising:
      detecting an impedance between the first and second electrical contacts;
      determining whether the detected impedance is less than a specified threshold;
      responsive to determining that the detected impedance is less than the specified threshold, providing an indication via the user interface; and
      subsequent to providing the indication via the user interface, detecting a voltage between the first electrical contact and the third electrical contact.

2. The wearable device of claim 1, wherein detecting a voltage between the first electrical contact and the third electrical contact comprises detecting an electrocardiogram.

3. The wearable device of claim 2, wherein the controller operations further comprise:
   determining a pulse rate based on the detected electrocardiogram.

4. The wearable device of claim 1, wherein the user interface comprises a display, and wherein the third electrical contact is disposed proximate to a peripheral edge of the display and at least partially encircles the display.

5. The wearable device of claim 1, further comprising an amplifier, wherein the amplifier is electrically coupled to the first electrical contact and the third electrical contact, wherein detecting a voltage between the first electrical contact and the third electrical contact comprises operating the amplifier to amplify the voltage.

6. The wearable device of claim 1, wherein detecting an impedance between the first and second electrical contacts comprises detecting first and second impedances at corresponding first and second points in time, wherein determining whether the detected impedance is less than a specified threshold comprises determining whether the second detected impedance is less than the specified threshold, and wherein the controller operations further comprise determining the specified threshold based on the first detected impedance.

7. The wearable device of claim 1, wherein the controller operations further comprise:
   responsive to determining that the detected impedance is greater than the specified threshold, providing an indication via the user interface.

8. The wearable device of claim 1, further comprising a capacitor electrically connected between the first and second electrical contacts, and wherein detecting an impedance between the first and second electrical contacts comprises:
   charging the capacitor during a first period of time;
   discharging the capacitor via the first and second electrical contacts during a second period of time; and
   determining a capacitor voltage across the capacitor at one or more points in time during the second period of time.

9. The wearable device of claim 8, wherein the controller operations further comprise detecting a capacitance between the first and second electrical contacts, and wherein detecting a capacitance between the first and second electrical contacts comprises electrically disconnecting the capacitor from at least one of the first electrical contact or the second electrical contact.

10. The wearable device of claim 1, wherein the controller operations further comprise determining whether the first and second electrical contacts are in contact with skin at the first external body surface based on the detected impedance.

11. A method comprising:
   detecting an impedance between a first electrical contact and a second electrical contact, wherein the first and second electrical contacts are disposed on a housing of a wearable device, wherein the wearable device comprises a mount configured to mount the housing to a first external body surface, wherein the first external body surface is a wrist location of a first arm of a wearer, and wherein the first and second electrical contacts are configured to contact skin at the first external body surface when the housing is mounted on the first external body surface;

determining whether the detected impedance is less than a specified threshold;

responsive to determining that the detected impedance is less than the specified threshold, providing an indication via a user interface of the wearable device, wherein the user interface is disposed on an outside surface of the housing; and subsequent to providing the indication via the user interface of the wearable device, detecting a voltage between the first electrical contact and a third electrical contact, wherein the third electrical contact is disposed on the housing of the wearable device, wherein the third electrical contact is configured to be contacted by skin of a second external body surface, and wherein the second external body surface is a location of a second arm of the wearer.

12. The method of claim 11, wherein detecting a voltage between the first electrical contact and the third electrical contact comprises detecting an electrocardiogram.

13. The method of claim 12, further comprising:
determining a pulse rate based on the detected electrocardiogram.

14. The method of claim 11, wherein detecting an impedance between the first and second electrical contacts comprises detecting first and second impedances at corresponding first and second points in time, wherein determining whether the detected impedance is less than a specified threshold comprises determining whether the second detected impedance is less than the specified threshold, and wherein the controller operations further comprise determining the specified threshold based on the first detected impedance.

15. The method of claim 11, further comprising:
responsive to determining that the detected impedance is greater than the specified threshold, providing an indication via the user interface of the wearable device.

16. The method of claim 11, further comprising:
determining whether the first and second electrical contacts are in contact with skin at the first external body surface based on the detected impedance.

17. The method of claim 11, wherein detecting an impedance between the first and second electrical contacts comprises:
charging a capacitor during a first period of time, wherein the capacitor is electrically connected between the first and second electrical contacts;
discharging the capacitor via the first and second electrical contacts during a second period of time; and
determining a capacitor voltage across the capacitor at one or more points in time during the second period of time.

18. The method of claim 17, further comprising:
detecting a capacitance between the first and second electrical contacts, wherein detecting a capacitance between the first and second electrical contacts comprises electrically disconnecting the capacitor from at least one of the first electrical contact or the second electrical contact.

* * * * *